(12) United States Patent
Manohar et al.

(10) Patent No.: US 12,376,588 B2
(45) Date of Patent: Aug. 5, 2025

(54) COMPOSITIONS AND METHODS FOR MODULATING IMMUNITY IN PLANTS

(71) Applicant: BOYCE THOMPSON INSTITUTE FOR PLANT RESEARCH, INC., Ithaca, NY (US)

(72) Inventors: Murli Manohar, Ithaca, NY (US); Frank Schroeder, Ithaca, NY (US)

(73) Assignee: BOYCE THOMPSON INSTITUTE FOR PLANT RESEARCH, INC., Ithaca, NY (US)

( * ) Notice: Subject to any disclaimer, the term of this patent is extended or adjusted under 35 U.S.C. 154(b) by 803 days.

(21) Appl. No.: 17/603,021

(22) PCT Filed: Apr. 17, 2020

(86) PCT No.: PCT/US2020/028656
§ 371 (c)(1),
(2) Date: Oct. 12, 2021

(87) PCT Pub. No.: WO2020/214901
PCT Pub. Date: Oct. 22, 2020

(65) Prior Publication Data
US 2022/0183291 A1    Jun. 16, 2022

Related U.S. Application Data

(60) Provisional application No. 62/835,179, filed on Apr. 17, 2019.

(51) Int. Cl.
*A01N 43/16* (2006.01)
*C07H 15/10* (2006.01)

(52) U.S. Cl.
CPC ............. *A01N 43/16* (2013.01); *C07H 15/10* (2013.01)

(58) Field of Classification Search
None
See application file for complete search history.

(56) References Cited

U.S. PATENT DOCUMENTS

| | | | |
|---|---|---|---|
| 8,318,146 B1 | 11/2012 | Teal et al. | |
| 10,136,595 B2 | 11/2018 | Klessig et al. | |
| 11,019,776 B2 | 6/2021 | Klessig et al. | |
| 2014/0364386 A1 | 12/2014 | Choe et al. | |

FOREIGN PATENT DOCUMENTS

| | | | |
|---|---|---|---|
| DK | 174489 B1 | 4/2003 | |
| WO | 2010/009241 A2 | 1/2010 | |
| WO | 2010/146062 A2 | 12/2010 | |
| WO | 2012/084858 A2 | 6/2012 | |
| WO | 2013/022985 A2 | 2/2013 | |
| WO | 2013/022997 A2 | 2/2013 | |
| WO | 2014/145380 A2 | 9/2014 | |

OTHER PUBLICATIONS

Hsueh, et al., "Nematode—Trapping Fungi Eavesdrop on Nematode Pheromones" Current Biology (2013) 23:83-86.
Ludewig, et al., "Ascaroside signaling in C. elegans" WormBook: the online review of C. elegans biology (2013) 1-22, wormbook.org.
Manosalva, et al., "Conserved nematode signalling molecules elicit plant defenses and pathogen resistance" Nat . Comm. (2015) 6:7795.
Von Reuss, et al., "Comparative Metabolomics Reveals Biogenesis of Ascarosides, a Modular Library of Small-Molecule Signals in C. elegans" J. Am. Chem. Soc. (2012) 134(3):1817-1824.
Choe, et asl., "Ascaroside Signaling is Widely Conserved among Nematodes" Current Biology (2012) 22:772-80.
Noguez, et al., "A novel ascaroside controls the parasitic life cycle of the entomopathogenic nematode Heterorhabditis bacteriophora" ACS Chem Biol. (2012) 7(6): 961-966.
Srinivasan, et al., "A blend of small molecules regulates both mating and development in Caenorhabditis elegans" Nature (2008) 454(7208):1115-1118.
Bose, et al., "Complex Small-Molecule Architectures Regulate Phenotypic Plasticity in a Nematode" Angew Chem Int Ed Engl. (2012) 51(50):12438-12443.
Kaplan, Fatma et al., "Interspecific Nematode Signals Regulate Dispersal Behavior", PLoS ONE (2012) 7(6): e38735.
Daudi, et al., "The Apoplastic Oxidative Burst Peroxidase in *Arabidopsis* is a Major Component of Pattern-Triggered Immunity" Plant Cell (2012) 24:275-287.
Jagdale, et al., "Entomopathogenic nematodes induce components of systemic resistance in plants: Biochemical and molecular evidence" Biological Control (2009) 51:102-109.
McConn, et al., "Jasmonate is essential for insect defense in *Arabidopsis*" Proc. Natl. Acad. Sci. (1997) 94:5473-5477.
Durrant, et al., "Systemic Acquired Resistance" Annu. Rev. Phyopathol. (2004) 42:185-209.
Von Reuss, et al., "Combinatorial chemistry in nematodes: modular assembly of primary metabolism-derived building blocks" Nat. Prod. Rep. (2015) 32:994-1006.
Zhang, et al., "Improved Synthesis for Modular Ascarosides Uncovers Biological Activity" Org. Lett. (2017) 19 (11):2837-2840.
Zhou, et al., "Biosynthetic tailoring of existing ascaroside phermones alters their biological function in C. elegans" eLife (2018) 7:e33286.
Manohar, et al., "Plant metabolism of nematode phermones mediates plant-nematode interactions" Nat. Comm. (2020) 11:208.

*Primary Examiner* — Patrick T Lewis
(74) *Attorney, Agent, or Firm* — Robert C. Netter, Jr.; Dann, Dorfman, Herrell & Skillman

(57) ABSTRACT

Compositions and methods for protecting an organism from a pathogen are disclosed.

22 Claims, 18 Drawing Sheets
Specification includes a Sequence Listing.

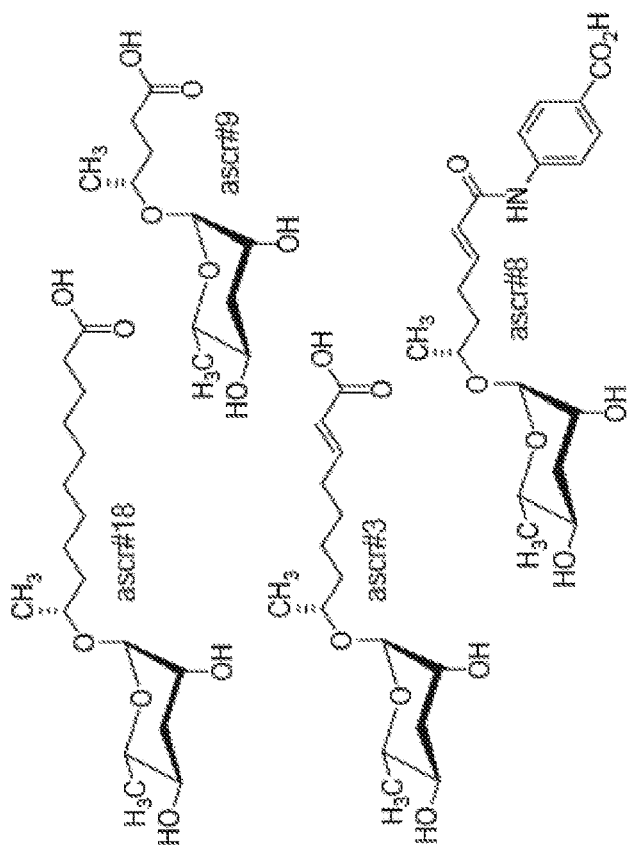
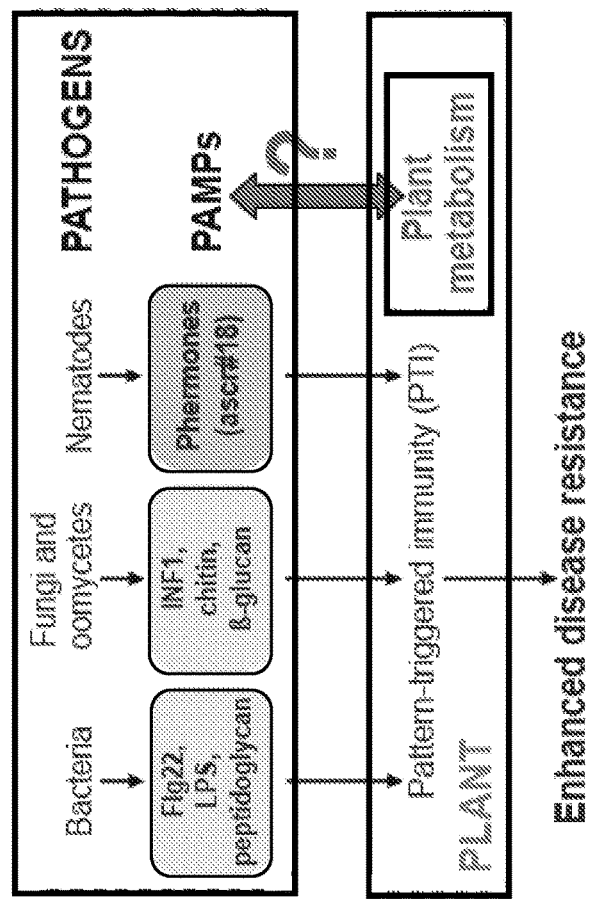
FIG. 1B
FIG. 1A

# COMPOSITIONS AND METHODS FOR MODULATING IMMUNITY IN PLANTS This application is a § 371 application of PCT/US2020/028656, filed Apr. 17, 2020, which in turn claims priority under 35 U.S.C. § 119(e) to U.S. Provisional Patent Application No. 62/835,179, filed Apr. 17, 2019. The foregoing applications are incorporated by reference herein.

This invention was made with government support under Grant No. 12217687 awarded by the National Institute of Food and Agriculture. The government has certain rights in the invention.

FIELD OF THE INVENTION

This invention relates to the fields of agriculture, small molecule pesticides and plant disease resistance. More specifically, the invention provides methods and compositions with utility in protecting crops from pathogens.

BACKGROUND OF THE INVENTION

Pathogens are responsible for enormous productivity losses in agriculture. Whether livestock, crop plants or even cultivation of organisms for fermentation processes, pathogens are a constant concern. In many cases, the available products to combat pathogens are less than optimal. Many existing products rely on toxic chemicals that have shown detrimental secondary effects. Older products are also becoming less efficacious due to the emergence of resistance as pathogens evolve mechanisms to tolerate heavily used products. In some cases, (e.g., agricultural uses of antibiotics or antiparasitic drugs) this can have negative consequences for human health as resistance developed in agricultural settings has the potential to transfer to human pathogens, and/or render human medicines less effective.

Against this background, the present invention provides effective methods and compositions for the control of pathogens that do not suffer these shortcomings.

SUMMARY OF THE INVENTION

While many examples are known of organisms producing defensive molecules to protect themselves against pathogens, the inventors have discovered an unexpected variation on this theme, whereby an organism threatened by a pathogen takes up a molecule produced and excreted by that pathogen and chemically modifies it to create a new molecule(s) that is then deployed as a chemical defense against the pathogen. Among other things, the present invention provides novel methods of protecting an organism from a pathogen. The provided methods may inhibit or reduce a pathogen's ability to infect the organism and/or decrease the likelihood of an infection of the organism by the pathogen. The methods of the instant invention may reduce or decrease a pathogen's ability to cause a disease or disorder in an organism and/or decrease the likelihood that the organism develops a disease or disorder caused by the pathogen.

In a particular embodiment, the method comprises contacting the target organism and/or its environment with a) a first ingredient with a chemical structure identical to a compound produced by a pathogen, and b) a second ingredient with a chemical structure identical to a metabolite produced by the target organism being protected; wherein the metabolite is the product of the target organism's metabolism of the compound produced by the pathogen. In a particular embodiment, the target organism is a plant. In a particular embodiment, the pathogen is a nematode. The compound produced by the pathogen may comprise an ascaroside (e.g., ascr #18). The metabolite produced by the organism may comprise a side-chain shortened analog or metabolite of the ascaroside (e.g., a side-chain shortened analog of ascr #18 such as ascr #9, ascr #10, and/or ascr #1). The first and second ingredients may be formulated in a single composition. In a particular embodiment, the mass ratio of the metabolite produced by the organism to the compound produced by the pathogen (e.g., ascr #18) is 1:10 or greater (e.g., at least 1:1, at least 2:1, at least 5:1, or at least 10:1). When the organism to be treated is a plant, the ingredients may be applied to any part of the plant (e.g., seed, root, and/or foliage) and/or the nearby soil. The treated organism may be protected against the pathogen (e.g., nematode) as well as at least one other pathogen (e.g., a virus, a bacteria, a fungus, an insect, and/or an oomycete).

Compositions comprising the above first and second ingredients are also encompassed by the instant invention. In a particular embodiment, the composition further comprises a carrier such as an agronomically acceptable carrier.

According to another aspect of the instant invention, methods for protecting an organism from a pathogen are provided comprising contacting the organism and/or its environment with an effective amount of an ingredient with a chemical structure identical to a compound produced by the pathogen, wherein the organism treated with the composition metabolizes the ingredient into a new compound with a structure different from the compound produced by the pathogen, and wherein the new compound has the effect of protecting the organism from the pathogen. In a particular embodiment, the ingredient does not itself have appreciable activity or has no activity in protecting the organism from the pathogen. In a particular embodiment, the organism is a plant. In a particular embodiment, the pathogen is a nematode. The compound produced by the pathogen may comprise an ascaroside (e.g., ascr #18). The new molecule produced by the organism may comprise a side-chain shortened analog or metabolite of the ascaroside (e.g., a side-chain shortened metabolite of ascr #18 such as ascr #9, ascr #10, and/or ascr #1). When the organism to be treated is a plant, the ingredient may be applied to any part of the plant (e.g., seed, root, and/or foliage) and/or the nearby soil. The treated organism may be protected against the pathogen (e.g., nematode) as well as at least one other pathogen (e.g., a virus, a bacteria, a fungus, an insect, and/or an oomycete).

BRIEF DESCRIPTION OF THE DRAWINGS

FIG. 1A provides a schematic of nematode-derived ascr #18 activating pattern-triggered immunity (PTI) in plants, similar to pathogen-associated molecular patterns (PAMPs) derived from other microbes. FIG. 1B provides examples of ascarosides discovered in *C. elegans* and other nematode species.

DETAILED DESCRIPTION OF THE INVENTION

Figure 1C:
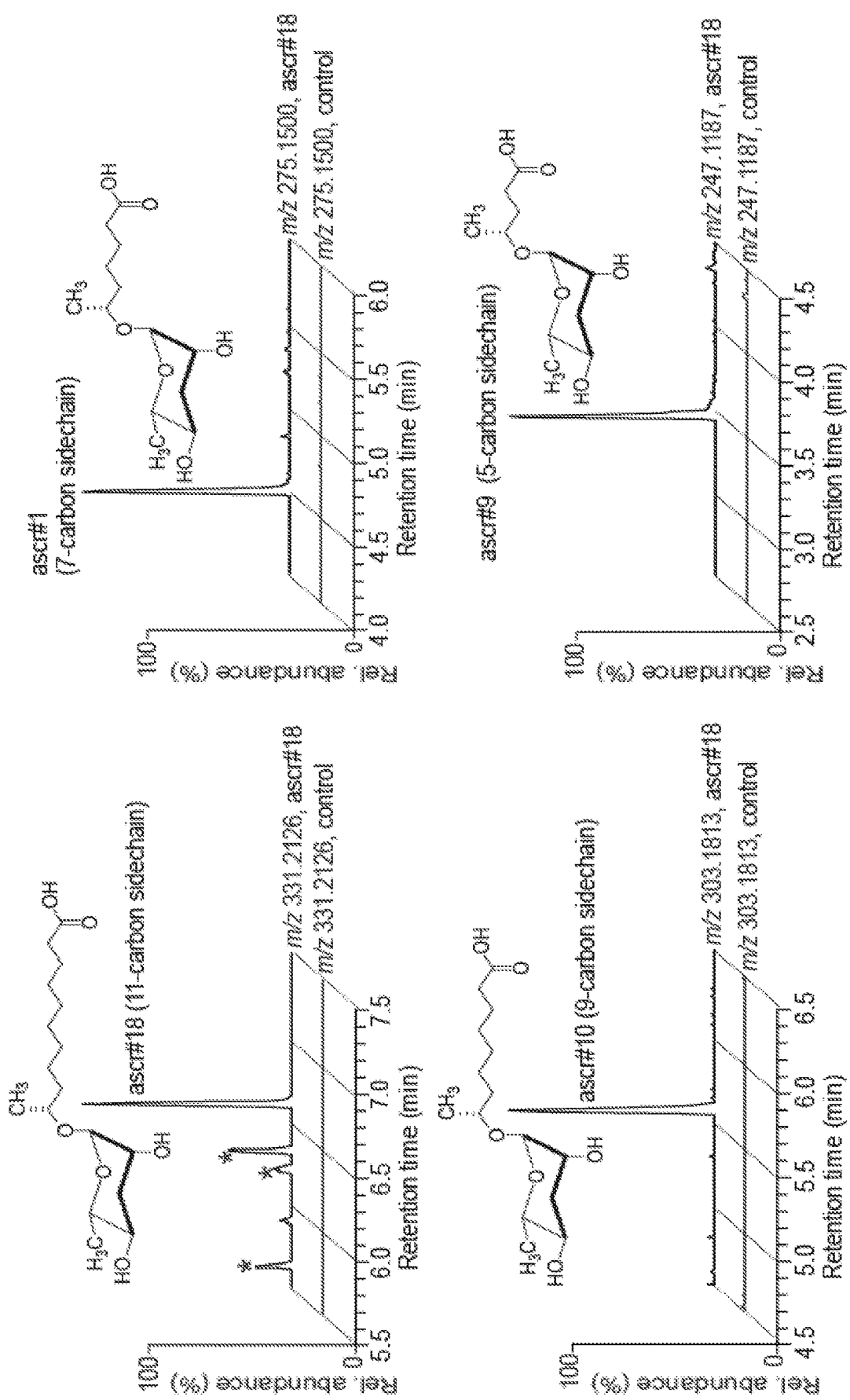
FIG. 1C provides liquid chromatography-mass spectrometry (LC-MS) analyses of *Arabidopsis* roots treated with 1 ascr #18 for 24 hours, showing extracted ion chromatograms [EIC] in electrospray ionization⁻ (ESI⁻) of ascr #18, ascr #10, ascr #1, and ascr #9. Peaks marked with an asterisk represent unrelated metabolites of similar m/z.

In accordance with the instant invention, methods of protecting an organism from a pathogen are provided. In a particular embodiment, the method comprises contacting the organism and/or its environment (e.g., its immediate environment) with an effective amount of a) a first ingredient with a chemical structure identical to a compound produced by the pathogen, and b) at least one second ingredient with a chemical structure identical to a metabolite produced by the organism being protected; wherein the metabolite is the product of the organism's metabolism of the compound produced by the pathogen. The organism and/or its environment may be contacted with the first and second ingredient at the same time and/or sequentially. In a particular embodiment, the first ingredient and second ingredient are contained within the same composition.

In accordance with another aspect of the instant invention, methods of protecting an organism from a pathogen are provided. In a particular embodiment, the method comprises contacting the organism and/or its environment (e.g., its immediate environment) with an effective amount of a composition comprising an ingredient with a chemical structure identical to a compound produced by the pathogen, wherein the organism treated with the composition metabolizes the ingredient into at least one new compound (e.g., a metabolite) with a structure different from the compound produced by the organism, and wherein the new compound(s) has the effect of protecting the organism from the pathogen.

With regard to the above methods, the compound produced by the pathogen may be a foreign (non-self) molecule or macromolecule to the organism being protected. Typically, the pathogen-produced compound is one that is secreted by the pathogen. In a particular embodiment, the pathogen-produced compound is a small molecule. The pathogen-produced compound applied according to the methods herein may be chemically synthesized, produced by fermentation, and/or isolated from the pathogen or a related organism (e.g., from a culture of the pathogen or a related organism).

In a particular embodiment, the pathogen-produced compound comprises the formula:

G-Lp-(C=O)—XR, wherein G represents a moiety selected from a sugar, an amino acid, a nucleic acid, a combination of two or more of these, and a derivative of any of these; Lp represents an optionally unsaturated chain comprising n carbon atoms, wherein n is an integer from 4 to 40 inclusive (e.g., a fatty acid-like side chain); X represents O, S, or NIR (particularly O); R is selected from —H, a metal ion, an optionally substituted moiety selected from $C_{1-12}$ aliphatic, $C_{1-12}$ heteroaliphatic, aromatic, heteroaromatic, and G-Lp-(C=O)—XR (e.g., a dimer or oligomer); and Ry is —H or an optionally substituted moiety selected from $C_{1-12}$ aliphatic, $C_{1-12}$ heteroaliphatic, aromatic, and heteroaromatic.

In a particular embodiment, G is an amino acid, a peptide, or a derivative thereof. In a particular embodiment, G is a sugar. In a particular embodiment, G is a sugar linked to Lp via a glycosidic bond. In a particular embodiment, G is a deoxy sugar, ascarylose, rhamnose, or a derivative thereof. In a particular embodiment, G has the formula

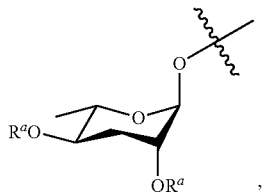

where $R^a$ is H, alkyl, acyl, a glycoside, a peptide, or a nucleoside, particularly H. In a particular embodiment, G is ascarylose.

In a particular embodiment, R is a $C_{1-6}$ aliphatic. In a particular embodiment, R is H. In a particular embodiment, Lp is an optionally substituted saturated or unsaturated chain (e.g., aliphatic chain). In a particular embodiment, Lp is an optionally substituted saturated or unsaturated chain containing 4 to 40 carbon atoms in its main chain (e.g., excluding any carbon atoms present on methyl or other groups branching from the main linear chain). In a particular embodiment, Lp is an optionally substituted, saturated or unsaturated chain containing 4 to 6, 4 to 8, 6 to 10, 6 to 12, 8 to 16, 10 to 20, 12 to 24, 16 to 24, or 20 to 32 carbon atoms in its main chain.

In a particular embodiment, Lp is an optionally substituted, saturated chain. In certain embodiments, Lp is an optionally substituted, saturated lipid containing 4 to 40 carbon atoms. In a particular embodiment, Lp is a saturated, optionally substituted chain containing 4 to 6, 4 to 8, 6 to 10, 6 to 12, 8 to 16, 10 to 20, 12 to 24, 16 to 24, or 20 to 32 carbon atoms in its main chain.

In a particular embodiment, Lp is a mono- or polyunsaturated, optionally substituted chain. In certain embodiments, Lp is a mono- or polyunsaturated, optionally substituted chain comprising 4 to 40 carbon atoms in its main chain. In certain embodiments, Lp is a mono-unsaturated, optionally substituted chain containing 4 to 6, 4 to 8, 6 to 10, 6 to 12, 8 to 16, 10 to 20, 12 to 24, 16 to 24, or 20 to 32 carbon atoms in its main chain. In certain embodiments, Lp is a polyunsaturated, optionally-substituted chain containing 4 to 6, 4 to 8, 6 to 10, 6 to 12, 8 to 16, 10 to 20, 12 to 24, 16 to 24, or 20 to 32 carbon atoms in its main chain.

In certain embodiments, Lp is a chain substituted at the carbon attached to G. In certain embodiments, Lp is a chain bearing a $C_{1-12}$ optionally substituted aliphatic group on the carbon atom attached to G. In certain embodiments, Lp is a chain bearing a $C_{1-8}$, a $C_{1-6}$, a $C_{1-4}$, or a $C_{1-3}$ optionally substituted aliphatic group on the carbon atom attached to G. In certain embodiments, Lp is a chain bearing an aliphatic moiety selected from the group of methyl, ethyl, n-propyl, i-propyl, n-butyl, sec-butyl, or allyl, on the carbon atom attached to G. In a particular embodiment, Lp has the formula —CHCH$_3$(CH$_2$)$_y$—, wherein y is an integer from 3 to 39. In a particular embodiment, Lp has the formula —CHCH$_3$(CH$_2$)$_y$—, wherein y is an integer from 3 to 6, from 4 to 8, from 6 to 10, from 6 to 12, from 8 to 16, from 10 to 20, from 12 to 24, from 16 to 24, or from 20 to 32 carbon atoms in its main chain. In a particular embodiment, Lp has the formula —CHCH$_3$(CH$_2$)$_8$—. In a particular embodiment, Lp has the formula —CHCH$_3$(CH$_2$)$_9$—. In a particular embodiment, Lp has the formula —CHCH$_3$(CH$_2$)$_{10}$—. In a particular embodiment, Lp has the formula —CHCH$_3$(CH$_2$)$_{12}$—. In a particular embodiment, Lp has the formula —CHCH$_3$(CH$_2$)$_7$—. In a particular embodiment, Lp has the formula —CHCH$_3$(CH$_2$)$_6$— and X is O. In a particular embodiment, Lp has the formula —CHCH$_3$(CH$_2$)$_8$—; X is O; and R is H.

In certain embodiments, Lp is a chain having geminal disubstitution on the carbon atom attached to G. In certain embodiments, Lp has a formula —C(CH$_3$)$_2$(CH$_2$)$_y$—, where y is as defined in the embodiments and examples herein.

In a particular embodiment, Lp is an unsaturated chain. In certain embodiments, Lp is an unsaturated chain having 1 to 3 sites of unsaturation. In certain embodiments, Lp is a mono-unsaturated chain. In certain embodiments, Lp has the formula —CHCH$_3$(CH$_2$)$_a$—CH=CH—(CH$_2$)$_b$—, wherein a and b are independently integers from 0 to 20 and the sum of a and b is 2 to 30. In a particular embodiment, Lp has the formula —CHCH$_3$(CH$_2$)$_z$CH=CH—, where z is an integer from 1 to 18. In a particular embodiment, Lp has the formula —CHCH$_3$(CH$_2$)$_z$CH=CH—, where z is an integer from 1 to 4, from 4 to 6, from 6 to 8, from 4 to 12, from 6 to 12, from 10 to 20, from 12 to 24, from 16 to 24. In a particular embodiment, Lp has the formula —CHCH₃(CH₂)₂CH=CH—. In a particular embodiment, Lp has the formula —CHCH₃(CH₂)₃CH=CH—. In a particular embodiment, Lp has the formula —CHCH₃(CH₂)₄CH=CH—. In a particular embodiment, Lp has the formula —CHCH₃(CH₂)₅CH=CH—. In a particular embodiment, Lp has the formula —CHCH₃(CH₂)₆CH=CH—. In a particular embodiment, Lp has the formula —CHCH₃(CH₂)₂CH=CH— and X is O. In a particular embodiment, Lp has the formula —CHCH₃(CH₂)₂CH=CH—; X is O; and R is H. In a particular embodiment, Lp has the formula —CHCH₃(CH₂)₄CH=CH— and X is O. In a particular embodiment, Lp has the formula —CHCH₃(CH₂)₄CH=CH—; X is O; and R is H.

In certain embodiments where Lp conforms to a formula with a substructure —CHCH₃CH₂ . . . , the chiral center (e.g. the underlined carbon atom in the substructure) is enantio-enriched. In certain embodiments, the chiral center is substantially enantiopure. In certain embodiments, the chiral center has the R configuration. In certain embodiments, the chiral center has the S configuration. In certain embodiments, the chiral center is present as a racemic (or diastereomeric) mixture.

In a particular embodiment, the pathogen-produced compound is an ascaroside. Examples of ascarosides suitable for the present invention include, but are not limited to:

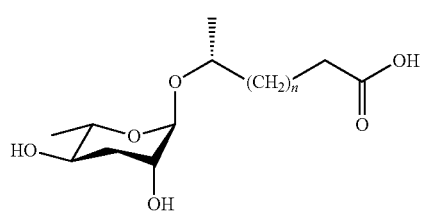

n = 6, ascr#16
n = 7, ascr#18
n = 8, ascr#20
n = 9, ascr#22
n = 10, ascr#24
n = 11, ascr#26

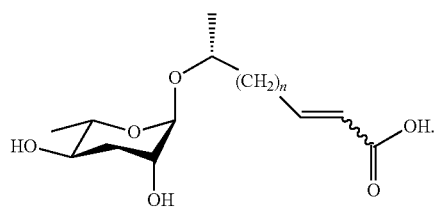

n = 5, ascr#15
n = 6, ascr#17
n = 7, ascr#19
n = 8, ascr#21
n = 9, ascr#23
n = 10, ascr#25

Further examples of ascarosides suitable for the present invention include, without limitation:

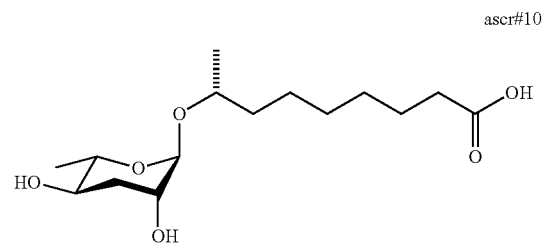

ascr#10

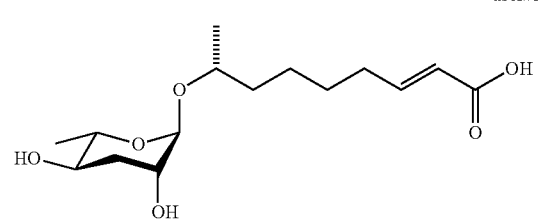

ascr#3

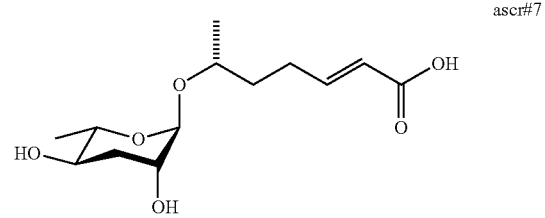

ascr#7

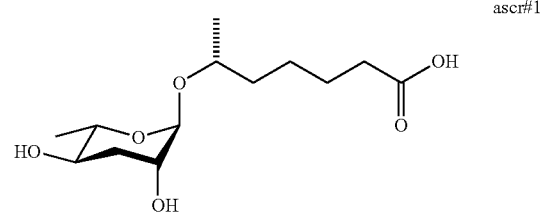

ascr#1

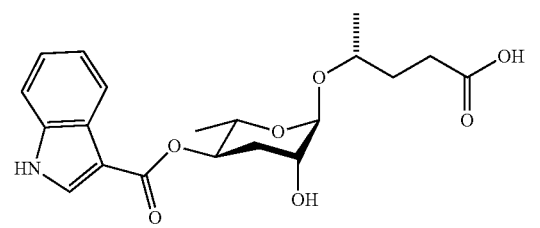

icas#9

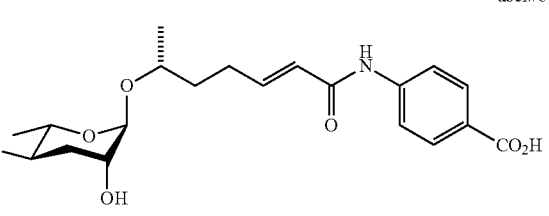

ascr#8

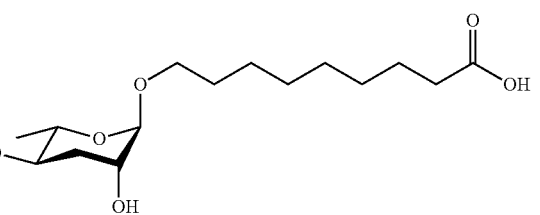

oscr#10

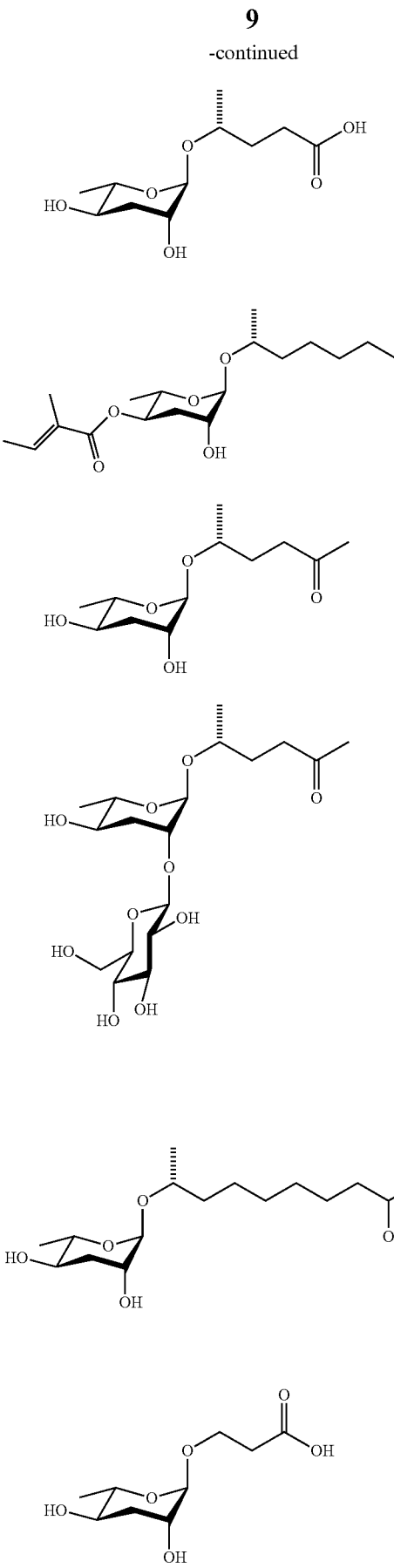
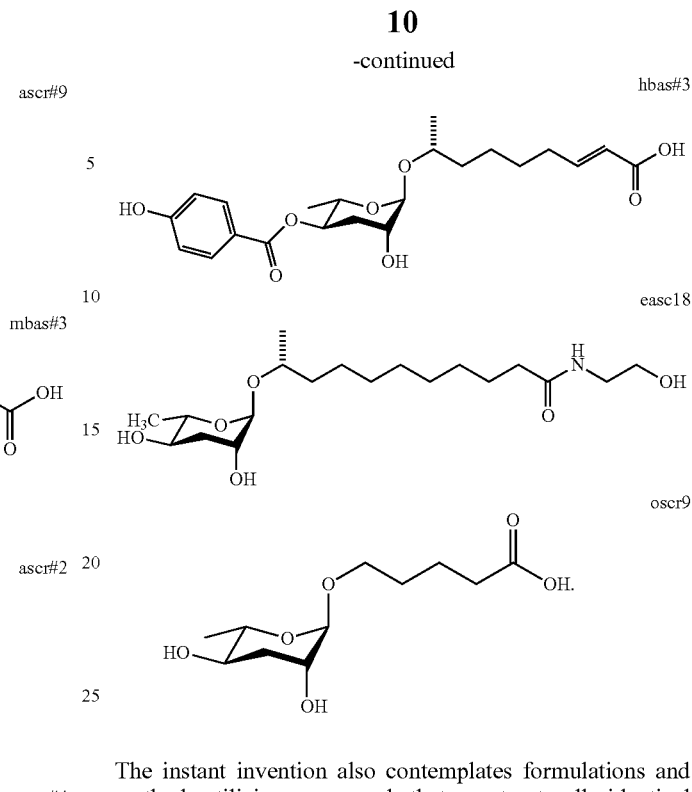

The instant invention also contemplates formulations and methods utilizing compounds that are structurally identical to the ascarosides depicted above except that the number of carbon atoms in the fatty acid-like side chain is changed (e.g., from between 3 and 32 carbons). Likewise, the instant invention encompasses compounds that are structurally identical to the ascarosides depicted above except that the identity of the substituents on the ascarylose oxygen atoms (e.g., on the hydroxyl groups at the 2- and 4-positions of the sugar) is changed. The instant invention also encompasses compounds that are structurally identical to the ascarosides depicted above except that the stereochemistry of one or more chiral centers is different (e.g., enantiomers, diastereomers or racemates of the depicted compounds). The instant invention also encompasses compounds that are structurally identical to the ascarosides depicted above except for the degree or pattern of deoxygenation of the sugar (e.g., compounds where one or both of the 3- and 6-positions of the sugar are not deoxygenated, and/or compounds where one or both of the 2- and 4-positions are deoxygenated).

In a particular embodiment, the pathogen-produced compound comprises ascr #18. The provided metabolite of the pathogen-produced compound may be chemically synthesized, produced by fermentation, and/or isolated from an organism exposed to the pathogen-produced compound. For example, the provided metabolite of the pathogen-produced compound may be produced by chemical and/or biological conversion of the pathogen-produced compound.

In a particular embodiment, the metabolite of the pathogen-produced compound has a formula:

$$G\text{-}Lp'\text{-}(C{=}O)\text{-}XR^m,$$

wherein, Lp' represents a chain comprising n' carbon atoms, wherein n' is an integer less than n in the pathogen-produced compound (e.g., a shortened fatty acid-like side chain); G and X are each as defined above and in the genera and subgenera herein, where each G and X may be the same or different from the corresponding moiety in the pathogen-produced compound; and $R^m$ is —H, a metal cation, or an optionally substituted moiety selected from $C_{1-12}$ aliphatic, $C_{1-12}$ heteroaliphatic, aromatic, heteroaromatic, a peptide, an amino acid or amino acid derivative, a sugar or sugar derivative, and a polysaccharide. In certain embodiments, $R^m$ is the same as R in the pathogen-produced compound.

In certain embodiments, $R^m$ comprises a sugar or sugar oligomer. In certain embodiments, the moiety —$XR^m$ is selected from the group consisting of:

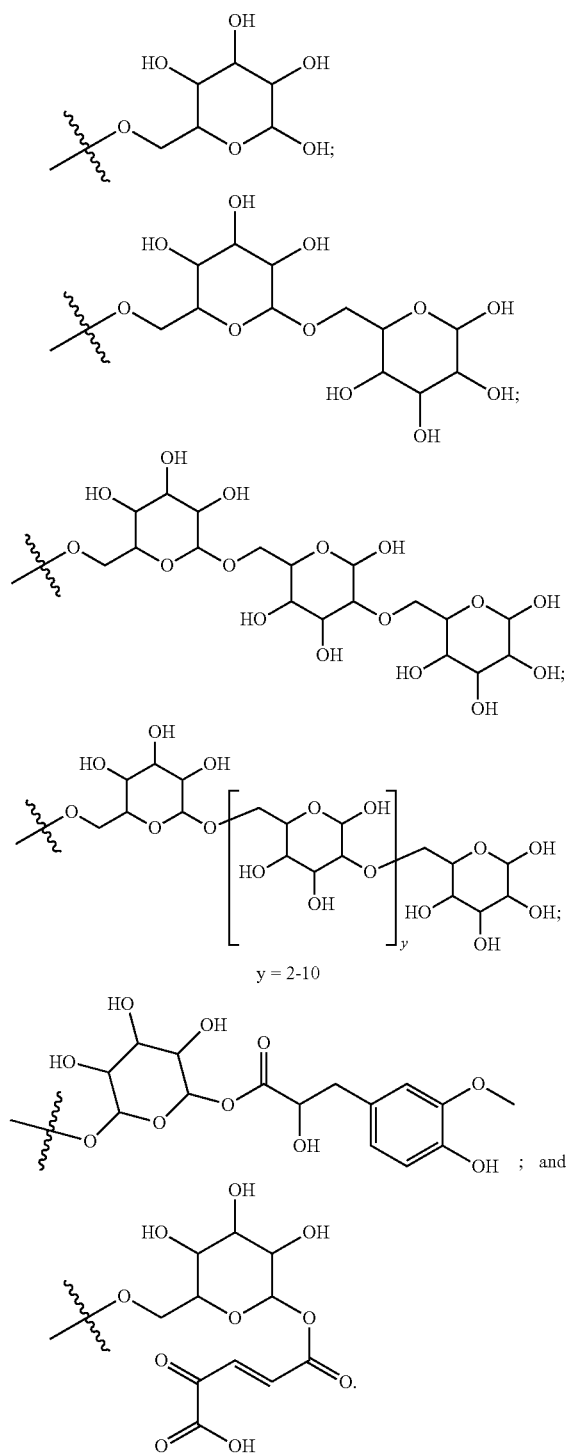

In certain embodiments, —$XR^m$ comprises an N-linked amino acid, an amino acid derivative, or a peptide. In certain embodiments, the moiety —$XR^m$ selected from the group consisting of:

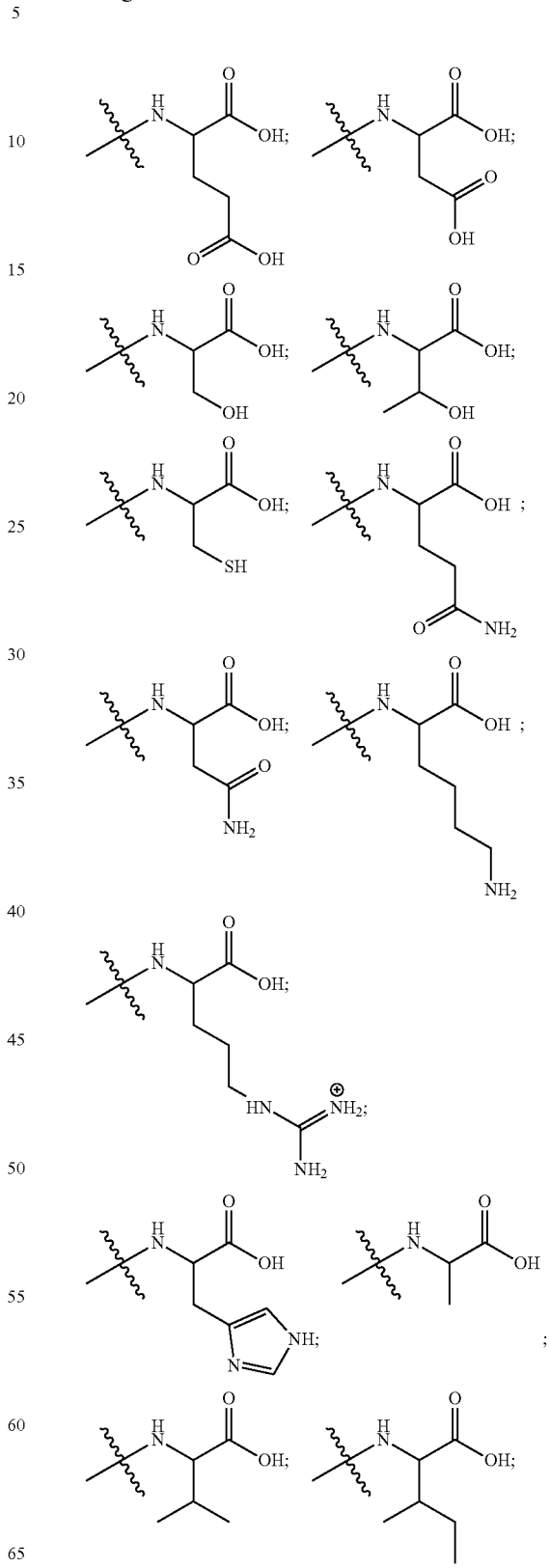

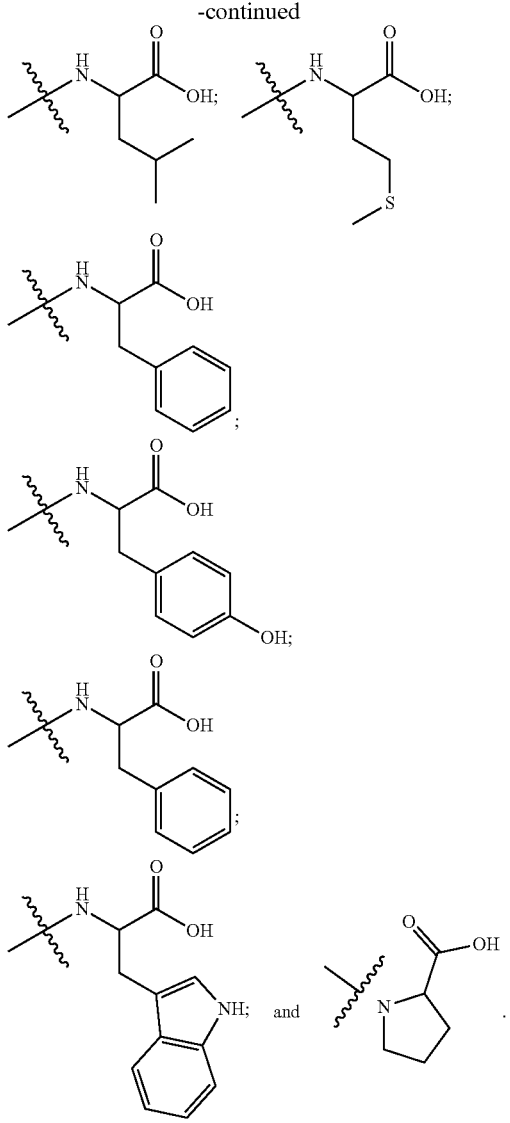

In certain embodiments, —XR$^m$ is:

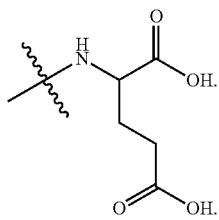 [SMILES: *NC(CCC(=O)O)C(=O)O]

In certain embodiments, Lp' in the metabolite is a chain comprising two fewer carbon atoms than Lp in the pathogen-produced compound. In certain embodiments, Lp' in the metabolite is a chain comprising four fewer carbon atoms than Lp in the pathogen-produced compound. In certain embodiments, Lp' in the metabolite is a chain comprising six fewer carbon atoms than Lp in the pathogen-produced compound. In certain embodiments, Lp' in the metabolite is a chain having fewer carbons and a different degree of unsaturation than Lp in the pathogen-produced compound. In certain embodiments, Lp in the pathogen-produced compound is an unsaturated chain and Lp' in the metabolite is a saturated chain. In certain embodiments, Lp in the pathogen-produced compound is a saturated chain and Lp' in the metabolite is an unsaturated chain. In certain embodiments, Lp' in the metabolite is a chain having fewer carbons than Lp in the pathogen-produced compound but having the same degree of unsaturation as Lp.

In a particular embodiment, Lp' is an optionally substituted, saturated or unsaturated chain. In a particular embodiment, Lp' is an optionally substituted, saturated or unsaturated chain containing 2 to 38 carbon atoms in its main chain (e.g. excluding any carbon atoms present on substituent groups branching from the main linear chain). In a particular embodiment, Lp' is an optionally substituted, saturated or unsaturated chain containing 2 to 4, 2 to 6, 4 to 8, 6 to 10, 6 to 12, 8 to 16, 10 to 20, 12 to 24, 16 to 24, or 18 to 30 carbon atoms in its main chain.

In a particular embodiment, Lp' is an optionally substituted, saturated chain. In certain embodiments, Lp' is an optionally substituted, saturated chain containing 2 to 38 carbon atoms. In a particular embodiment, Lp' is a saturated, optionally substituted chain containing 2 to 4, 4 to 6, 4 to 8, 6 to 10, 6 to 12, 8 to 16, 10 to 20, 12 to 24, 16 to 24, or 18 to 30 carbon atoms in its main chain.

In a particular embodiment, Lp' is a mono- or polyunsaturated, optionally substituted chain. In certain embodiments, Lp' is a mono- or polyunsaturated, optionally substituted chain comprising 4 to 40 carbon atoms in its main chain. In certain embodiments, Lp' is a mono-unsaturated, optionally substituted chain containing 2 to 4, 4 to 6, 4 to 8, 6 to 10, 6 to 12, 8 to 16, 10 to 20, 12 to 24, 16 to 24, or 18 to 30 carbon atoms in its main chain. In certain embodiments, Lp' is a polyunsaturated, optionally substituted chain containing 2 to 4, 4 to 6, 4 to 8, 6 to 10, 6 to 12, 8 to 16, 10 to 20, 12 to 24, 16 to 24, or 18 to 30 carbon atoms in its main chain.

In certain embodiments, Lp' is a chain substituted at the carbon attached to G. In certain embodiments, Lp' is a chain bearing a $C_{1-12}$ optionally substituted aliphatic group on the carbon atom attached to G. In certain embodiments, Lp' is a chain bearing a $C_{1-8}$, a $C_{1-6}$, a $C_{1-4}$, or a $C_{1-3}$ optionally substituted aliphatic group on the carbon atom attached to G. In certain embodiments, Lp' is a chain bearing an aliphatic moiety selected from the group of methyl, ethyl, n-propyl, i-propyl, n-butyl, sec-butyl, or allyl, on the carbon atom attached to G. In a particular embodiment, Lp' has the formula —CHCH$_3$(CH$_2$)$_{y'}$, wherein y' is an integer from 3 to 39. In a particular embodiment, Lp' has the formula —CHCH$_3$(CH$_2$)$_{y'}$, wherein y' is an integer from 3 to 6, from 4 to 8, from 6 to 10, from 6 to 12, from 8 to 16, from 10 to 20, from 12 to 24, from 16 to 24, or from 20 to 32 carbon atoms in its main chain. In certain embodiments, where Lp in the pathogen-produced compound is substituted, Lp' in the metabolite is identically substituted. In certain embodiments, where Lp in the pathogen-produced compound is substituted at the carbon attached to G, Lp' in the metabolite is identically substituted.

In a particular embodiment, Lp in the pathogen-produced compound has the formula —CHCH$_3$(CH$_2$)$_8$— and Lp' in the metabolite has a formula selected from: —CHCH$_3$(CH$_2$)$_6$—, —CHCH$_3$(CH$_2$)$_4$—, —CHCH$_3$(CH$_2$)$_2$—, or a combination of any two or more of these. In a particular embodiment, Lp has the formula —CHCH$_3$(CH$_2$)$_8$— and Lp' has the formula —CHCH$_3$(CH$_2$)$_6$—. In a particular embodiment, Lp has the formula —CHCH$_3$(CH$_2$)$_8$— and Lp' has the formula —CHCH$_3$(CH$_2$)$_4$—. In a particular embodiment, Lp has the formula —CHCH$_3$(CH$_2$)$_8$— and Lp' has the formula —CHCH$_3$(CH$_2$)$_2$—. In a particular embodiment, Lp has the formula —CHCH$_3$(CH$_2$)$_8$—, Lp' has the formula —CHCH$_3$(CH$_2$)$_6$— and X is O. In a particular embodiment, Lp has the formula —CHCH$_3$(CH$_2$)$_8$—; Lp' has the formula —CHCH$_3$(CH$_2$)$_8$—; X is O; and R is H.

In a particular embodiment, Lp in the pathogen-produced compound has the formula —CHCH$_3$(CH$_2$)$_9$— and Lp' in the metabolite has a formula selected from: —CHCH$_3$(CH$_2$)$_7$—, —CHCH$_3$(CH$_2$)$_5$—, —CHCH$_3$(CH$_2$)$_3$—, —CHCH$_3$CH$_2$—, or a combination of any two or more of these. In a particular embodiment, Lp has the formula —CHCH$_3$(CH$_2$)$_9$— and Lp' has the formula —CHCH$_3$(CH$_2$)$_7$—. In a particular embodiment, Lp' has the formula —CHCH$_3$(CH$_2$)$_9$— and Lp' has the formula —CHCH$_3$(CH$_2$)$_5$—. In a particular embodiment, Lp' has the formula —CHCH$_3$(CH$_2$)$_9$— and Lp' has the formula —CHCH$_3$(CH$_2$)$_3$—. In a particular embodiment, Lp' has the formula —CHCH$_3$(CH$_2$)$_9$— and Lp' has the formula —CHCH$_3$CH$_2$—.

In a particular embodiment, Lp in the pathogen-produced compound has the formula —CHCH$_3$(CH$_2$)$_{10}$— and Lp' in the metabolite has a formula selected from: —CHCH$_3$(CH$_2$)$_8$—, —CHCH$_3$(CH$_2$)$_6$—, —CHCH$_3$(CH$_2$)$_4$—, —CHCH$_3$(CH$_2$)$_2$—, or a combination of any two or more of these. In a particular embodiment, Lp has the formula —CHCH$_3$(CH$_2$)$_{10}$— and Lp' has the formula —CHCH$_3$(CH$_2$)$_8$—. In a particular embodiment, Lp has the formula —CHCH$_3$(CH$_2$)$_{10}$— and Lp' has the formula —CHCH$_3$(CH$_2$)$_6$—. In a particular embodiment, Lp has the formula —CHCH$_3$(CH$_2$)$_{10}$— and Lp' has the formula —CHCH$_3$(CH$_2$)$_4$—. In a particular embodiment, Lp has the formula —CHCH$_3$ (CH$_2$)$_{10}$— and Lp' has the formula —CHCH$_3$(CH$_2$)$_2$—. In a particular embodiment, Lp has the formula —CHCH$_3$(CH$_2$)$_{10}$— and Lp' has the formula —CHCH$_3$(CH$_2$)$_6$— and X is O. In a particular embodiment, Lp has the formula —CHCH$_3$(CH$_2$)$_{10}$— and Lp' has the formula —CHCH$_3$(CH$_2$)$_6$—; X is O; and R is H.

In a particular embodiment, Lp' comprises an unsaturated chain. In certain embodiments, Lp' is an unsaturated chain having 1 to 3 sites of unsaturation. In certain embodiments, Lp' is a mono-unsaturated chain. In certain embodiments, Lp' has the formula —CHCH$_3$(CH$_2$)$_a$—CH=CH—(CH$_2$)$_b$—, wherein at least one of the integers a' or b' is less than a or b in Lp of the pathogen-produced compound.

In a particular embodiment, Lp in the pathogen-produced compound has the formula —CHCH$_3$(CH$_2$)$_2$CH=CH— and Lp' in the metabolite is selected from the group consisting of: —CHCH$_3$CH=CH—, —CHCH$_3$(CH$_2$)$_4$—, —CHCH$_3$(CH$_2$)$_2$—, —CHCH$_3$—, and combinations of any two or more of these.

In a particular embodiment, Lp has the formula —CHCH$_3$(CH$_2$)$_4$CH=CH— and Lp' has a formula selected from the group consisting of: —CHCH$_3$(CH$_2$)$_2$CH=CH—, —CHCH$_3$CH=CH—, —CHCH$_3$(CH$_2$)$_6$—, —CHCH$_3$(CH$_2$)$_4$—, —CHCH$_3$(CH$_2$)$_2$—, —CHCH$_3$—, and combinations of any two or more of these. In a particular embodiment, Lp has the formula —CHCH$_3$(CH$_2$)$_4$CH=CH— and Lp' has the formula —CHCH$_3$(CH$_2$)$_2$CH=CH—. In a particular embodiment, Lp' has the formula —CHCH$_3$(CH$_2$)$_2$CH=CH—; and X is O. In a particular embodiment, Lp' has the formula —CHCH$_3$(CH$_2$)$_2$CH=CH—; X is O; and R is H.

In certain embodiments where Lp' conforms to a formula with a substructure —CHCH$_3$ . . . , the chiral center (e.g. the underlined carbon atom in the substructure) is enantio-enriched. In certain embodiments where the pathogen-produced compound comprises an Lp chain containing a chiral center and the chiral center is also present in Lp' in the metabolite, the chiral center in Lp' has the same conformation as the corresponding stereocenter in Lp. In certain embodiments, the metabolite of the pathogen-produced compound has the same chain Lp as the pathogen-produced compound but differs from the pathogen produced compound in the identity of the moiety —XR. In certain embodiments, such metabolites have a structure:

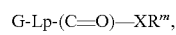

G-Lp-(C=O)—XR''', wherein, each of G-, -Lp-, X, and R''' is as defined above and in the genera and subgenera herein and characterized in that the moiety —XR''' in the metabolite has a structure that is different from the moiety —XR in the pathogen-produced compound.

In certain embodiments, the atom X in the moiety —XR''' has the same identity as atom X in the pathogen produced compound. In certain embodiments the atom X is oxygen in both instances.

In certain embodiments, the atom X in the moiety —XR''' is different from atom X in the pathogen produced compound. In certain embodiments X is oxygen in the pathogen-produced compound and is nitrogen or sulfur in the metabolite. In certain embodiments X is oxygen in the pathogen-produced compound and is nitrogen in the metabolite. In certain embodiments X is nitrogen in the pathogen-produced compound and is oxygen or sulfur in the metabolite. In certain embodiments X is nitrogen in the pathogen-produced compound and is oxygen in the metabolite.

In certain embodiments, —XR in the pathogen produced compound is —OH, and —XR''' in the metabolite is selected from the group consisting of:

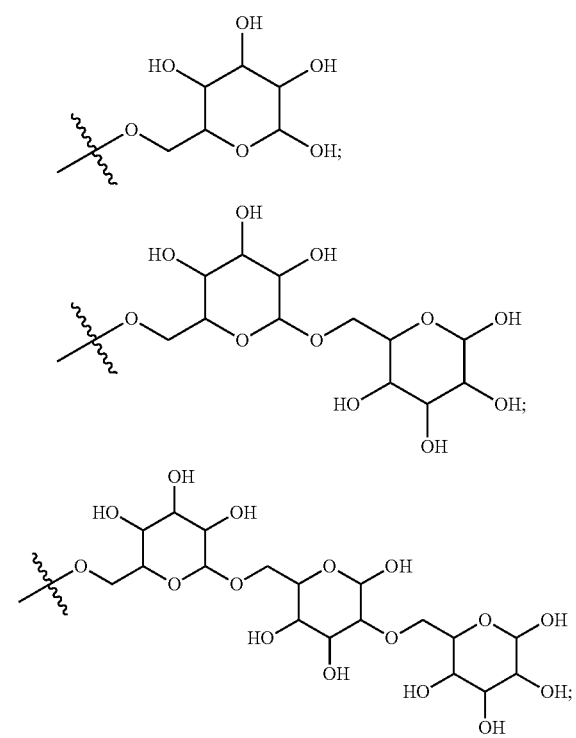

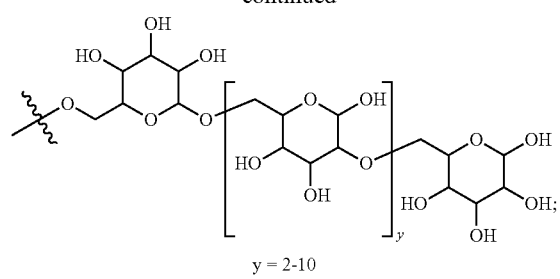
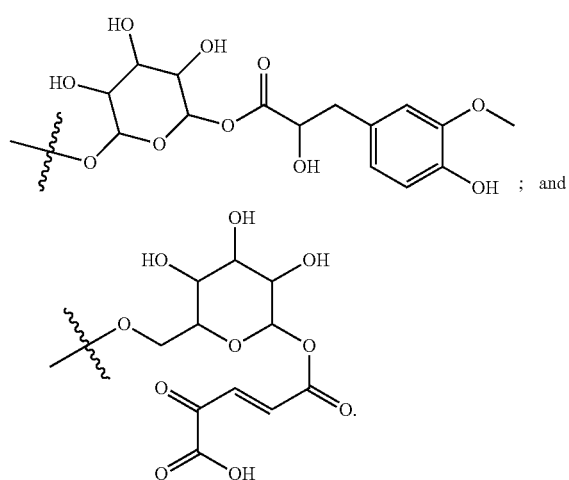
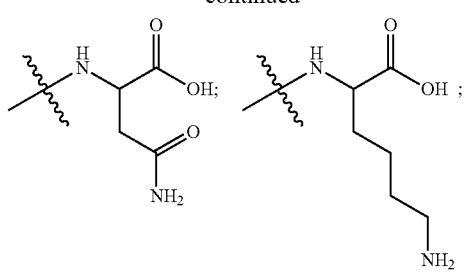
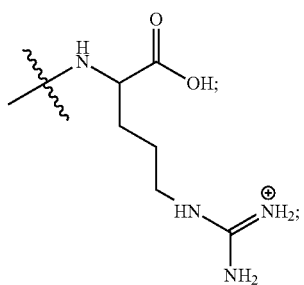
In certain embodiments, —XR in the pathogen produced compound is —OH, and —XR$^m$ in the metabolite is selected from the group consisting of:
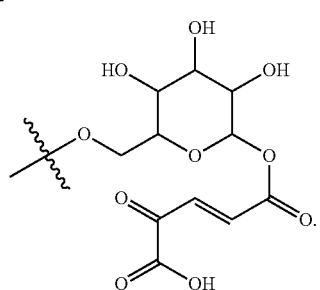
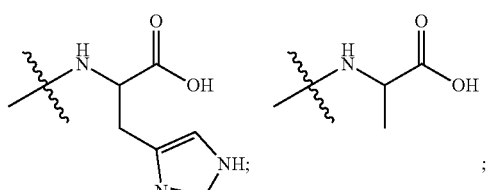
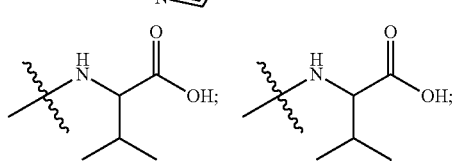
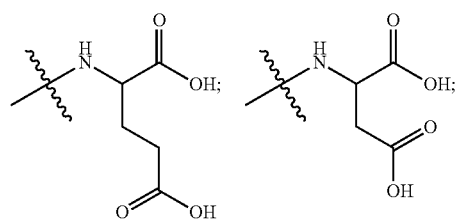
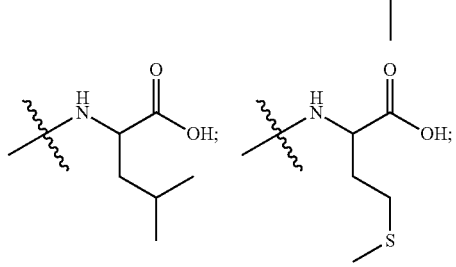
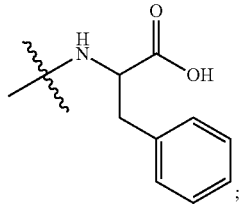
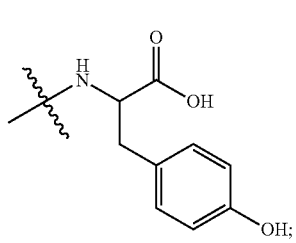

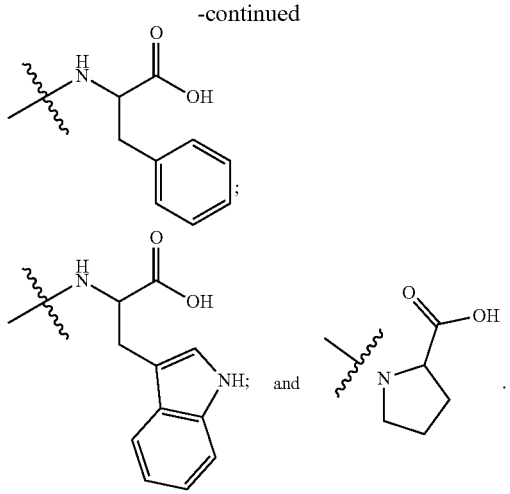

In certain embodiments, —XR in the pathogen produced compound is —OH, and X— in the metabolite is:

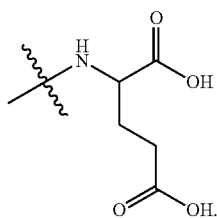 [SMILES: *NC(CCC(=O)O)C(=O)O]

In a particular embodiment, the metabolite of the pathogen-produced compound is an ascaroside. In a particular embodiment, the metabolite of the pathogen-produced compound is a side-chain shortened homolog or analog of a pathogen-produced ascaroside. In a particular embodiment, the metabolite of the pathogen-produced compound is a side-chain shortened metabolite or analog of ascr #18. In a particular embodiment, the metabolite of the pathogen-produced compound is ascr #10, ascr #1, ascr #9, or a combination of any two or more of these. In a particular embodiment, the pathogen-produced compound is ascr #18, and the metabolite of the pathogen-produced compound is ascr #10, ascr #1, ascr #9 or a combination of any two or more of these. In a particular embodiment, the pathogen-produced compound is ascr #18, and the metabolite of the pathogen-produced compound is a derivative of ascr #10, ascr #1, ascr #9 or a combination of any two or more of these. In certain embodiments, such derivatives comprise modification of the ascarylose. In certain embodiments, such derivatives comprise esters, thioesters, or amides of the fatty acid sidechain. In a particular embodiment, the metabolite of the pathogen-produced compound is at least ascr #10 or comprises ascr #10. In a particular embodiment, the metabolite of the pathogen-produced compound is at least ascr #1 or comprises ascr #1. In a particular embodiment, the metabolite of the pathogen-produced compound is at least ascr #9 or comprises ascr #9.

The methods of the instant invention can be used to protect any organism from a pathogen. In a particular embodiment, the organism to be protected is different than the pathogen (e.g., a different species). In a particular embodiment, the organism is a plant or plant cell. Plants and plant cells to be treated using the compositions and methods described herein include, but are not limited to: tobacco, tomato, barley, soybean, potato, sweet potato, yam, cassava, cotton, flax, soybean, strawberry, sugar beet, corn, rice, wheat, rye, oat, sorghum, millet, canola, bean, pea, chickpea, lentil, apple, banana, pear, cherry, peach, plum, apricot, almond, grape, kiwi, mango, melon, papaya, walnut, hazelnut, pistachio, raspberry, blackberry, loganberry, blueberry, cranberry, orange, lemon, grapefruit, tangerine, lettuce, carrots, onions, broccoli, cabbage, avocado, and cocoa. In certain embodiments, the plant is a grain. In certain embodiments, the plant is selected from the group consisting of corn, soybean, wheat, canola, and rice. In certain embodiments, the plant is a vegetable crop. In certain embodiments, the plant is an ornamental.

The methods of the instant invention can be used to protect an organism from any pathogen. For example, the methods of the instant invention can be used to protect an organism from a virus, bacteria, fungus, oomycete, insect, and/or nematode. In a particular embodiment, the pathogen is a nematode. The methods of the instant invention may protect the organism (e.g., plant) from the pathogen that produces the pathogen-produced compound in addition to at least one other pathogen that may not produce the compound. For example, the method may comprise a compound produced by nematodes, and protect a plant against nematodes and at least one other pathogen such as a virus, bacteria, fungus, insect, and/or oomycete. In a particular embodiment, the plant-pathogen combination is selected from a plant-pathogen system described in Klessig et al. (J. Phytopathol. (2019) 1-8; incorporated herein by reference). Examples of pathogens include without limitation: *Pseudomonas syringae* pv. *tabaci*, *Pseudomonas syringae* pv. *tomato*, *Phytophthora infestans*, *Phytophthora sojae*, Soybean Mosaic Virus, *Xanthomonas oryzae* pv. *oryzae*, *Xanthomonas translucens*, *Fusarium culmorum*, *Cochliobolus heterostrohpus*, *Rhizoctonia solani*, *Botrytis cinerea*, *Zymoseptoria tritici*, *Blumeria graminis* f. sp. *hordei*, the cyst nematode *Heterodera schachtii* and *Heterodera glycines*, the root-knot nematodes *Meloidogyne incognita* and *Meloidogyne hapla*, the lesion nematode *Pratylenchus brachyurus*, and turnip crinkle virus.

As stated hereinabove, the methods of the instant invention comprise contacting the organism or its environment (e.g., its immediate environment (e.g., with regard to a plant, to the soil, particularly within the area of soil containing the root system of the plant)) with a pathogen-produced compound and, optionally, a metabolite of the pathogen-produced compound. The compounds of the instant invention may be administered to any part of the organism. When the organism is a plant, the compounds of the instant invention may be administered to any part of the plant. For example, the compounds of the instant invention may be administered to a root, stem, leaf, seed and/or flower of the plant. In a particular embodiment, the compounds of the instant invention are administered to a root of the plant. In a particular embodiment, the compounds of the instant invention are administered to a seed of the plant. In a particular embodiment, the compounds of the instant invention are administered to seed grain of a plant intended to be planted for purposes of producing or propagating the plant. In a particular embodiment, the compounds of the instant invention are administered to a leaf of the plant.

The treatment of plants and/or soil with the compounds and formulations described herein may be carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

In a particular embodiment, the compounds of the instant invention are administered by foliar application. In a particular embodiment, the compounds of the instant invention are administered through the root system via the soil (systemic action) by drenching the locus of the plant with a liquid preparation or by incorporating the substances into the soil in solid form, e.g., in the form of granules comprising the substances compounded with carriers (soil application). In rice cultivations, these granules may be dispensed over the flooded paddy field. The compounds of the invention may also be applied to tubers or seed grain, for example, by soaking, spraying or drenching the seed grain or tubers in a liquid composition or by coating the tubers or seed grain with a solid composition.

Depending on the plant species or plant cultivars, their location and growth conditions (e.g., soils, climate, vegetation period, and/or diet), the treatment according to the invention may also result in super-additive or synergistic effects. Thus, for example, reduced application rates and/or a widening of the activity spectrum and/or an increase in the activity of the substances and compositions to be used, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products that exceed the effects which were actually to be expected may occur.

The compounds of the instant invention may be used alone or contained in a composition with a carrier. For example, the compounds described herein may be formulated together with an agronomically acceptable carrier. The term "agronomically acceptable carrier" includes any carrier suitable for administration to a plant or soil. For example, customary excipients in formulation techniques, such as solutions (e.g., directly sprayable or dilutable solutions), aqueous solutions, emulsions, (e.g., emulsion concentrates and diluted emulsions), wettable powders, suspensions, soluble powders, powders, dusts, pastes, soluble powders, granules, suspension-emulsion concentrates, encapsulation into polymeric materials, coatable pastes, natural and synthetic materials impregnated with active compound and microencapsulations in polymeric substances. These formulations are produced in a known manner, for example by mixing the compounds with agronomically acceptable carrier, such as liquid solvents or solid carriers, optionally with the use of surfactants, including emulsifiers, dispersants, and/foam-formers. In a particularly embodiment, the agronomically acceptable carrier is synthetic or nan-natural.

If the agronomically acceptable carrier is water, the composition may also comprise auxiliary solvents such as organic solvents. Suitable liquid solvents include, for example, aromatics (e.g., xylene, toluene and alkylnaphthalenes); chlorinated aromatics or chlorinated aliphatic hydrocarbons (e.g., chlorobenzenes, chloroethylenes and methylene chloride); aliphatic hydrocarbons (e.g., cyclohexane); paraffins (e.g., petroleum fractions, mineral and vegetable oils); alcohols (e.g., butanol or glycol and also their ethers and esters); ketones (e.g., acetone, methyl ethyl ketone, methyl isobutyl ketone and cyclohexanone) and strongly polar solvents (e.g., dimethylformamide and dimethyl sulphoxide). It is preferred that non toxic carriers be used in the methods of the present invention.

Suitable solid agronomically acceptable carriers include, for example, ammonium salts and ground natural minerals (e.g., kaolins, clays, talc, chalk, quartz, attapulgite, montmorillonite and diatomaceous earth); ground synthetic minerals (e.g., highly disperse silica, alumina and silicates); crushed and fractionated natural rocks (e.g., calcite, marble, pumice, sepiolite and dolomite); synthetic granules of inorganic and organic meals; and granules of organic material (e.g., sawdust, coconut shells, maize cobs, and tobacco stalks). Suitable emulsifiers and foam-formers include, for example, nonionic and anionic emulsifiers (e.g., polyoxyethylene fatty acid esters, polyoxyethylene fatty alcohol ethers, for example, alkylaryl polyglycol ethers, alkylsulphonates, alkyl sulphates and arylsulphonates) and protein hydrolysates.

Suitable dispersants include, for example, lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be also used in the formulations. Other additives may include, for example, mineral and vegetable oils.

Colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc may also be included in the agronomically acceptable carrier.

The compounds or compositions of the instant invention may be administered to the plant and/or soil by any techniques known in the art, including, for example, spraying, atomizing, dusting, scattering, coating or pouring. One of skill in the art would be able to determine the appropriate technique for administration without undue experimentation according the specific pathogen to be combated, the specific chemical composition and formulation of the compound being employed, the method of applying the compound/formulation, and the locus of treatment.

The compositions disclosed herein generally comprise between 0.001 and 95% by weight of active compound(s), particularly between 0.001 and 1%. Favorable application rates are, in general, 0.001 g to 100 g of active substance(s) (AS) per hectare (ha), for example, 0.001 g to 0.01 g AS/ha, 0.01 g to 0.1 g AS/ha, 0.1 g to 0.5 g AS/ha, 0.5 g to 1 g AS/ha, 1 g to 5 g AS/ha, or 5 g to 25 g AS/ha. For application of tubers or seed grain, dosages of 0.001 mg to 100 mg active substance per kg of seed grain or tubers may be used, for example or 0.001 to 0.01 mg/kg, 0.01 to 0.05 mg/kg, 0.05 to 0.1 mg/kg, 0.1 to 0.5 mg/kg, 0.5 to 1 mg/kg, 1 to 5 mg/kg, or 5 to 1 mg/kg.

In accordance with another aspect of the instant invention, compositions for performing the methods of the instant invention are provided. Specifically, the compositions may be used to protect a target organism from a pathogen, as described herein. In a particular embodiment, the composition comprises a) a first ingredient with a chemical structure identical to a compound produced by the pathogen, and b) a second ingredient with a chemical structure identical to a metabolite which is the product of the target organism's metabolism of the compound produced by the pathogen. In a particular embodiment, the first ingredient (pathogen-produced compound) and second ingredient (metabolite of the pathogen-produced compound) are as described in the genera, subgenera, and examples herein.

The first ingredient (pathogen-produced compound) and second ingredient (metabolite of the pathogen-produced compound) may be contained within the composition at a defined mass ratio. For example, the mass ratio of the second ingredient (metabolite of the pathogen-produced compound) to the first ingredient (pathogen-produced compound) may be 1:1 or greater (e.g., at least or about 2:1, at least or about 5:1, or at least or about 10:1).

In a particular embodiment, the compositions comprise a first ingredient having the formula:

G-Lp-(C=O)—XR, where each of G, Lp, X, and R is as defined above and in the genera and subgenera herein.

In a particular embodiment, the provided compositions comprise a first ingredient having the formula:

G-Lp-(C=O)—XR, in combination with a second ingredient comprising one or more compounds conforming to the formula:

G-Lp'—(C=O)—XR''', where each of G, Lp, X, and R, Lp', X, and R''' is as defined above and in the genera and subgenera herein, wherein Lp' has fewer carbons than Lp.

In a particular embodiment, the provided compositions comprise a pathogen-produced compound that is an ascaroside and a metabolite of the pathogen-produced compound that is a side-chain shortened metabolite or analog of the pathogen-produced ascaroside. In a particular embodiment, the pathogen-produced compound is ascr #18 and the metabolite of the pathogen-produced compound is a side-chain shortened metabolite or analog of ascr #18. In a particular embodiment, the pathogen-produced compound is ascr #18 and the metabolite of the pathogen-produced compound is ascr #10, ascr #1, ascr #9, or a mixture of any two or more of these.

In a particular embodiment, the composition comprises a mass ratio of chain shortened analogs/metabolites of ascr #18 (e.g., ascr #10, ascr #1, and/or ascr #9) to ascr #18 of 1:1 or greater (at least or about 2:1, at least or about 5:1, or at least or about 10:1). In a particular embodiment, the composition comprises a mass ratio of chain shortened analogs/metabolites of ascr #18 (e.g., ascr #10, ascr #1, and/or ascr #9) to ascr #18 of about 5:1 to about 15:1, particularly about 7:1 to about 13:1 or about 9:1 to about 11:1. In a particular embodiment, the composition comprises a mass ratio of ascr #9 to ascr #18 of 1:1 or greater (at least or about 2:1, at least or about 5:1, or at least or about 10:1). In a particular embodiment, the composition comprises a mass ratio of ascr #9 to ascr #18 of about 5:1 to about 15:1, particularly about 7:1 to about 13:1 or about 9:1 to about 11:1.

Definitions

The following definitions are provided to facilitate an understanding of the present invention.

The term "ascaroside" refers to any of a group of glycolipids, containing the sugar ascarylose, found in nematodes.

The term "pathogen" refers to any bacterium, fungus, oomecyte, virus, nematode (e.g., cyst or root knot nematode), or insect, with pathogenic effects on the plant.

The term "substantially pure" refers to a preparation comprising at least 50-60% by weight of a given material (e.g., small molecule, nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC-MS analysis, and the like).

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Carriers can be sterile liquids, such as water and oils, including those of petroleum, animal, vegetable or synthetic origin. Water or aqueous saline solutions and aqueous dextrose and glycerol solutions can be employed as carriers.

As used herein, the term "small molecule" refers to a substance or compound that has a relatively low molecular weight (e.g., less than 4,000, less than 2,000, particularly less than 1 kDa or 800 Da). Typically, small molecules are organic.

The term "aliphatic" refers to a non-aromatic hydrocarbon-based moiety. Aliphatic compounds can be acyclic (e.g., linear or branched) or cyclic moieties (e.g., cycloalkyl) and can be saturated or unsaturated (e.g., alkyl, alkenyl, and alkynyl). Aliphatic compounds may comprise a mostly carbon main chain (e.g., 1 to about 30 carbons) and comprise heteroatoms and/or substituents (see below). The term "alkyl," as employed herein, includes saturated or unsaturated, straight or branched chain hydrocarbons containing 1 to about 30 carbons in the normal/main chain, particularly 24 or fewer carbon atoms (e.g., methyl, ethyl, n-propyl, ipropyl, n-butyl, s-butyl, t-butyl, n-pentyl, i-pentyl, n-hexyl, and the like). Branched alkyl means that one or more lower alkyl groups such as methyl, ethyl, or propyl are attached to a linear alkyl chain. The hydrocarbon chain of the alkyl groups may be interrupted with one or more heteroatom (e.g., oxygen, nitrogen, or sulfur). An alkyl (or aliphatic) may, optionally, be substituted (e.g. with fewer than about 8, fewer than about 6, or 1 to about 4 substituents). The term "lower alkyl" or "lower aliphatic" refers to an alkyl or aliphatic, respectively, which contains 1 to 3 carbons in the hydrocarbon chain. Alkyl or aliphatic substituents include, without limitation, alkyl (e.g., lower alkyl), alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or NHRC(=O)—, wherein R is an alkyl), urea (—$NHCONH_2$), alkylurea, aryl, ether, ester, thioester, nitrile, nitro, amide, carbonyl, carboxylate and thiol.

"Alkenyl" means an alkyl, as defined above, containing at least one double bond between adjacent carbon atoms. Alkenyls include both cis and trans isomers. Branched alkenyl means that one or more lower alkyl groups such as methyl, ethyl, or propyl are attached to a linear alkenyl chain.

The term "halogen" refers to fluoro, chloro, bromo, and iodo. The term "halo alkyl" refers to a branched or straight-chain alkyl as described above, substituted with one or more halogens.

The term "acyl" refers to a group of general formula —C(O)R, wherein R is an aliphatic or alkyl. In a particular embodiment, the term "acyl" refers to groups of from 1 to 8 carbon atoms of a straight, branched, or cyclic configuration, saturated, unsaturated, or aromatic, and combinations thereof, attached to the parent structure through a carbonyl functionality. One or more carbons in the acyl residue may be replaced by nitrogen, oxygen, or sulfur as long as the point of attachment to the parent remains at the carbonyl. Examples include acetyl (Ac), benzoyl, propionyl, isobutyryl, t-butoxycarbonyl, benzyloxycarbonyl, and the like.

Amino acids can be in D- or L-configuration. Suitable amino acids include α-amino acids, β-amino acids, γ-amino acids, δ-amino acids, and ε-amino acids, and include not only natural amino acids (i.e., those found in biological systems, including the twenty amino acids found in natural proteins), but also naturally-occurring variants of such amino acids, as well as synthetic amino acids and their analogues known to those skilled in the art. Exemplary amino acids include, without limitation: the twenty natural amino acids, 4-hydroxyproline, hydroxyysine, demosine, isodemosine, 3-methylhistidine, norvalin, beta-alanine, gamma-aminobutyric acid, citrulline, homocysteine, homoserine, ornithine, and methionine sulfone.

The term "aromatic" or "aryl" means an aromatic monocyclic or multi-cyclic (polycyclic) ring system of 6 to about 19 carbon atoms, for instance, about 6 to about 10 carbon atoms, and includes arylalkyl groups. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl. The term "heteroaromatic" or "heteroaryl" means an aromatic monocyclic or multi-cyclic ring system of about 5 to about 19 ring atoms, for instance, about 5 to about 10 ring atoms, in which one or more of the atoms in the ring system is/are element(s) other than carbon, for example, nitrogen, oxygen, and/or sulfur. In the case of multi-cyclic ring systems, only one of the rings needs to be aromatic for the ring system to be defined as "heteroaromatic" or "heteroaryl". Exemplary "heteroaromatic" or "heteroaryl" may contain about 5 or 6 ring atoms. Representative heteroaryls include, but are not limited to, purinyl, pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, quinolinyl, isoquinolinyl, quinazolinyl, cinnolinyl, pthalazinyl, quinoxalinyl, and the like.

The term "fatty acid" generally refers to a carboxylic acid with an aliphatic tail (chain). The aliphatic chain can be between about 2 and about 36 carbon atoms in length. Fatty acids can be saturated, unsaturated, or polyunsaturated. The aliphatic chain can be a linear or a branched chain. The term "fatty acid" may be used herein to refer to a "fatty acid derivative" which can include one or more different fatty acid derivatives, or mixtures of fatty acids derivatives. Exemplary fatty acids include, without limitation, unsaturated fatty acids, saturated fatty acids, and diacids; mono-, di-, and tri-glycerides of ascarosides that have a carboxylic acid functionality; hydroxy acids, co hydroxy acids, co-I hydroxy acids, di-hydroxy fatty acids (e.g., dihydroxy fatty acids that are omega- or omega-1 hydroxylated, as well as alpha- or beta-hydroxylated fatty acids).

The term "sugar" includes mono-, di-, tri-, and oligosaccharides. The sugar may be naturally occurring or synthetic. In a particular embodiment, the sugar is a monosaccharide. In a particular embodiment, the monosaccharide is cyclic. In a particular embodiment, the monosaccharide comprises 3-10 carbon atoms. The monosaccharide can be in D- or L-configuration. In a particular embodiment, the monosaccharide is a deoxy sugar.

The following examples are provided to illustrate certain embodiments of the invention. They are not intended to limit the invention in any way.

EXAMPLES

Herein, it is shown that the ascaroside ascr #18, a pheromone secreted by plant-pathogenic nematodes (e.g., a pathogen-produced compound of formula G-Lp-(C=O)—XR, where G- is the glycoside of ascarylose; -Lp- is a chain having the formula —CHCH$_3$(CH$_2$)$_8$—, where the underlined stereocenter has the R configuration; X is O; and R is —H) is taken up by plants which then convert it to a mixture of metabolites having formula G-Lp'—(C=O)—XR, where G- is the glycoside of ascarylose; -Lp'- is a mixture comprising —CHCH$_3$(CH$_2$)$_6$—, —CHCH$_3$(CH$_2$)$_4$—, and —CHCH$_3$(CH$_2$)$_2$—, where the underlined stereocenter has the R configuration; X is O; and R is —H). It is further demonstrated that when one or more of these metabolites is formulated in a mixture with the original pathogen-produced compound, the mixture effectively repels pathogenic nematodes and reduces plant infection by these nematodes. Comparative metabolomics of plant tissues and excretions revealed that plants metabolize ascr #18 into side-chained shortened metabolites via beta oxidation by peroxisomal oxidases. This is supported by observations that a plant (an *Arabidopsis* mutant) that is genetically defective in two peroxisomal acyl-CoA oxidases does not metabolize ascr #18.

While the molecular structures of specific microbial and nematode-derived pathogen associated molecular patterns (PAMPs) have been previously identified, it was unexpected to find that editing of the PAMPs by metabolism in the organism targeted by the pathogen could generate a new chemical signal that repels the pathogen producing the PAMP.

The inventors first investigated whether plants metabolize ascarosides produced by plant pathogenic nematodes. It was discovered that the pathogen-produced compound ascr #18 is rapidly metabolized into ascarosides with shortened fatty acid side chains. A screen of fatty acid metabolism mutants in *Arabidopsis* revealed that chain shortening of ascr #18 proceeds via peroxisomal β-oxidation (pβo). *Arabidopsis* mutants incapable of metabolizing ascr #18 into shorter-chained ascarosides do not show an ascr #18-mediated defense against pathogenic nematodes, though protection against microbial pathogens conferred by ascr #18 remains unaffected. Metabolomic analyses of plant root exudates revealed that the chain-shortened metabolites of the pathogen-produced ascarosides (ascr #18) are excreted via the roots, which in combination with the pathogen-produced compound deter nematodes. These results show that contrary to expectations, organisms can actively partake in pathogen chemical communications by biochemical editing of pathogen-produced compounds and deploying them to deter infection by the pathogen.

Methods

Plant Material and Growth Conditions

Unless otherwise stated, *Arabidopsis thaliana* ecotype Col-0, tomato (*Solanum lycopersicum*) cultivar M82, and wheat (*Triticum aestivum*) cultivar Kanzler plants were grown in a growth chamber under a 16-hour light/8-hour dark (22° C.) regime with 70% relative humidity.

Plant Genotypes

*Arabidopsis thaliana* mutant genotypes in the Col-0 background, ibr10-1, ech2-1, ibr10-1ech2-1, and acx1-2acx5-1, were obtained from Rice University (Houston, TX) (Strader, et al. (2011) Plant Cell 23:984-999; Adham, et al. (2005) Plant J. 41:859-874).

Sample Extraction

Plant tissues were immediately frozen in liquid nitrogen and ground to a fine powder and extracted with 350 μL mixture of water/methanol/chloroform (1:2:1) for 12 hours at 4° C., with shaking at 220 rpm. The extracts were dried in vacuo, resuspended in 100-200 μL of 80% methanol and analyzed by LC/MS. For root tissues, seedlings were extensively washed three times with the excess amount of distilled water and dried on filter paper. The root tissues from 40 seedlings were pooled in one tube and then similarly extracted. Mixed stage *C. elegans* culture extract was prepared as described (Panda, et al. (2017) Angew Chem. Int. Ed. Engl. 56(17):4729-4733).

Mass Spectrometric Analysis

High resolution LC-MS analysis was performed on a Dionex™ 3000 UPLC system coupled with a Thermo Q Exactive™ high-resolution mass spectrometer as described (Artyukhin, et al. (2018) J. Am. Chem. Soc. 140(8):2841-2852; Panda, et al. (2017) Angew Chem. Int. Ed. Engl. 56(17):4729-4733). Metabolite extracts were separated using water-acetonitrile gradient using Agilent ZORBOX Eclispse XDB-C18 rapid resolution column (2.1 mm×150 mm, particle size 1.8-micron) maintained at 40° C. Solvent A: 0.1% formic acid in water; Solvent B: 0.1% formic acid in acetonitrile. AB gradient started at 5% B for 1.5 minutes after injection and increased linearly to 100% B at 12.5 minutes, using a flow rate of 0.5 ml/minute. Mass spectrometer parameters: spray voltage 2.9 kV; capillary temperature 320° C.; prober heater temperature 300° C.; sheath, auxiliary, and spare gas 70, 2, and 0, respectively; S-lens RF level S5, resolution 140 000 at m/z 200, AGC target $1×10^6$. The instrument was calibrated in negative and positive modes with m/z range 200 to 1000 using calibration solutions (Thermo-Fisher). Ascarosides were detected in negative ionization mode as $[M-H]^-$ and MS/MS spectra and retention times confirmed by comparison with known standards.

Feature Detection and Characterization

LC-MS raw files obtained from at least triplicate sets of plant tissues, unless indicated otherwise, were converted into the mzXML data format (centroid mode) using MSConvert (ProteoWizard), followed by analysis using a customized XCMS R-script based on matchFilter centWave algorithm to extract all features (Tautenhahn, et al. (2012) Anal. Chem. 84(11):5035-9). The resulting table of all detected features was used to compare the peak area of ascarosides. Identified ascarosides masses were put on the inclusion list for MS/MS (ddMS2) characterization and checked for the presence of ascaroside diagnostic mass (73.028). Parameters of MS/MS were MS1 resolution 70 000, maximum injection time 250 ms, MS2 resolution 35 000, maximum injection time 125 ms, isolation window 0.8 m/z, stepped normalization collision energy 20, 40, 60 or 20, 40, 80, under fill ratio 2.0%, dynamic exclusion 1 s.

Ascaroside Treatments

Ascarosides were dissolved in ethanol to prepare millimolar stock solutions. Final aqueous ascaroside dilutions were prepared fresh on the day of the experiment. Aqueous control solutions contained equal amounts of ethanol (less than 0.1% for most experiments). For root treatments, plant pots were placed in a tray containing control solution or water supplemented with ascr #18. For seedling treatment, plant growth media was supplemented with control or ascr #18-containing solutions. *Arabidopsis* growth medium contained 2.15 g/L Murashige & Skoog salts (Sigma-Aldrich), 10 g/L sucrose, and the pH was adjusted to 6.0 using KOH. Tomato and wheat growth media contain 4.3 g/L Murashige & Skoog salts, 30 g/L sucrose, 0.112 g/L Gamborg's B5 vitamin solution (Sigma-Aldrich), and the pH was adjusted to 5.5 using KOH. For solid growth media, 8 g/L agar (Sigma-Aldrich) was added to the above formulations before autoclaving. For chemotaxis population assays, aqueous ascaroside-containing solutions or control solutions were applied on either side of the plates.

Plant Infection Assays

For bacterial growth assays, 3 leaves of 3.5 weeks-old *Arabidopsis* plant roots pretreated for 24 hours with ascr #18 or mock solutions were syringe infiltrated with a suspension of virulent Pst DC3000 in 10 mM $MgCl_2$ at a density of $1×10^5$ colony-forming units (cfu)/mL. For bacterial counts, three leaf discs (diameter of 0.7 cm) from each of the three inoculated leaves were collected from each plant three days post-inoculation and placed into a tube. Bacterial recovery was done using 1 mL of 10 mM $MgCl_2$, serial dilutions, and subsequent plating was performed as described (Tian, et al. (2009) Plant Physiol. 150:815-824). Briefly, 20 μL from each tube was transferred to the wells of a microtitre plate containing 180 μL of 10 mM $MgCl_2$, and serial 10-fold dilutions were prepared using a multi-channel pipette. 5 μL from each dilution was spotted onto a 150 mm Petri plate of Luria-Bertani broth (BD Biosciences) medium containing 34 μg/ml rifampicin and 15 g/L bacto agar (BD Biosciences), and the plates were incubated at 28° C. Bacterial counts were performed 48 hours post incubation.

For *Arabidopsis* nematode infection assays, *Meloidogyne incognita* was propagated and hatched as described (Manosalva, et al. (2015) Nat. Commun. 6:7795). Briefly, *M. incognita* were propagated on tomato (*Solanum lycopersicum* cv. Tiny Tim). *M. incognita* eggs were then isolated from egg masses on tomato roots with 0.5% sodium hypochlorite and rinsed with water on a 25-μm sieve. Collected nematode eggs were treated in a solution of 0.02% sodium azide for 20 minutes, and then hatched over water containing 1.5 mg/mL gentamycin sulfate and 0.05 mg/mL nystatin at room temperature on a Baermann pan for three days. Hatched second-stage juveniles (J2) were collected, surface sterilized with an aqueous solution of mercuric chloride (0.004%) and sodium azide (0.004%) for 10 minutes, and rinsed three times with sterile distilled water. Surface-sterilized J2 were resuspended in 0.1% agarose at a concentration of 10 J2 larvae per 10 μL and used for *Arabidopsis* inoculation. *Arabidopsis* ecotype Col-0 seeds were surface sterilized and planted in six-well plates containing Knop medium supplemented with 2% sucrose. Plants were grown at 24° C. under 16-hour-light/8-hour-dark conditions. Two mL of aqueous ≤0.1% ethanol solution containing various concentrations of ascr #18 or the aqueous ≤0.1% ethanol only control solution was added to each well containing 10 day-old seedlings. After 48 hours of pretreatment, the solution was removed and approximately 300 freshly hatched, surface-sterilized juveniles (J2) of *M. incognita* were inoculated on the roots of each seedling. Galls forts. *incognita* were counted under a microscope six weeks after inoculation.

Worm Attraction Assays

Figure 6A:
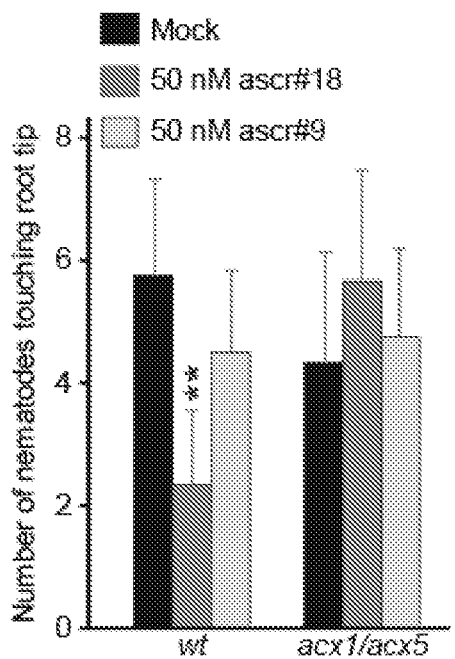
FIG. 6A provides a graph of the number of nematodes touching the root tips of *Arabidopsis* wildtype and acxlacx5 treated with 50 nM ascr #18 or ascr #9 for 48 hours before transfer into 12-well plates containing Pluronic® F-127 gel with ~200 freshly hatched *M. incognita* J2 larvae. Larvae touching the terminal part of roots were counted at 6 hours after seedling transfer. Data are average±s.d. (n=12).
Figure 6B:
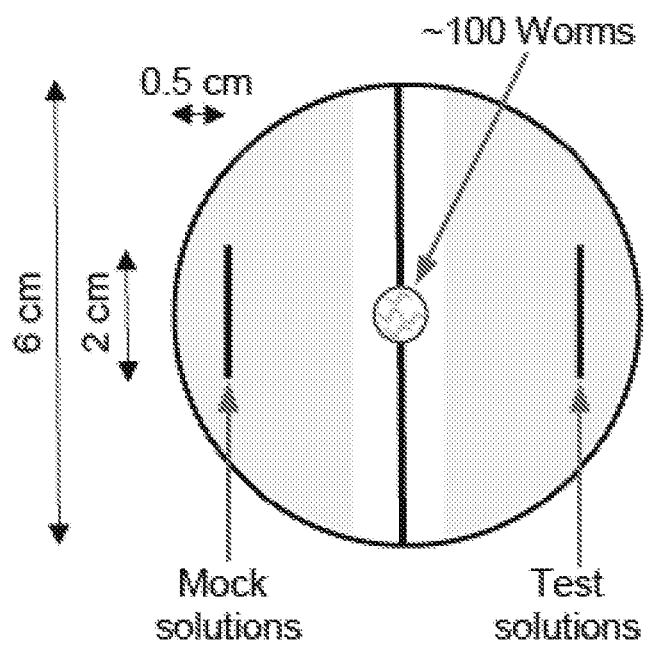
FIG. 6B provides a schematic of a Petri dish as shown in the plate layout. For FIG. 6C, the indicated concentrations of ascr #18, ascr #9, or ascr #18/ascr #9 mixtures were placed on one side with mock solutions on the other side of the 6-cm Petri dish. Subsequently, approximately 100 freshly hatched *M. incognita* J2 larvae were placed in the center of the plate. Larvae in the indicated scoring areas were counted after 4 hours. Data are averages±s.d. (n=12), P≤0.003; two-tailed t-test.

Chemotaxis plates were prepared by pouring 8 mL of 2% bacto-agar (BD Biosciences) into 6-cm Petri dishes. Immediately before adding worms, 10 μL of control solution or ascaroside-containing solutions were placed on opposite sides of the plate as shown in FIG. 6B. About 100 worms were placed in the center of the plates. The plates were then placed in a 25° C. incubator for 4 hours before counting the worms on both sides of the plates. Worms that remained in the center 0.5-cm-wide strip were not counted.

RNA Analyses

For each replicate, total RNA from *Arabidopsis* leaves were isolated from a pool of one leaf from each of three plants. For the seedling RNA analyses, *Arabidopsis* roots were collected from 30-40 seedlings for each replicates. Total RNA was isolated using Qiagen RNeasy® Plant Mini Kit (Qiagen) according to the manufacturer's instructions. DNAse treatment was done using DNA-Free™ Kit (Ambion) following the manufacturer's instructions. First-strand cDNA was synthesized from 1 μg of total RNA using M-MLV reverse transcriptase (Promega) and amplified using gene-specific primers (Manosalva, et al. (2015) Nat. Commun. 6:7795; Table 1).

TABLE 1

Primers

| Primer Name | Sequence | SEQ ID NO |
| --- | --- | --- |
| AtPR-1 F | TCGTCTTTGTAGCTCTTGTAGGTG | 1 |
| AtPR-1 R | TAGATTCTCGTAATCTCAGCTCT | 2 |
| AtPDF1.2-F | TCATGGCTAAGTTTGCTTCC | 3 |
| AtPDF1.2-R | AATACACACGATTAGCACC | 4 |
| AtFRK1-fw | TGCAGCGCAAGGACTAGAG | 5 |
| AtFRK1-rv | ATCTTCGCTTGGAGCTTCTC | 6 |
| AtPHI-fw | TTGGTTTAGACGGGATGGTG | 7 |
| AtPHI-rv | ACTCCAGTACAAGCCGATCC | 8 |
| AtUBQ-fw | GGCCTTGTATAATCCCTGATGAATAAG | 9 |
| AtUBQ-rv | AAAGAGATAACAGGAACGGAAACATAG | 10 |
| AtPR4-F | CTGGACCGCCTTCTGCGGG | 11 |
| AtPR4-R | AGCCTCCGTTGCTGCATTGGT | 12 |
| AtAOS-F | TCTTCTCTTCGCCACGTGC | 13 |
| AtAOS-R | GGTTATGAACTTGATGACCCGC | 14 |
| AtLOX2-F | TTGCTCGCCAGACACTTGC | 15 |
| AtLOX2-R | GGGATCACCATAAACGGCC | 16 |

For quantitative real-time PCR (qRT-PCR), transcripts were amplified using SYBR® Premix Ex-Taq™ (Takara) from 2.5 μL of 5×-diluted cDNA in a total 20 μL reaction using 0.1 μL of 100 μM gene-specific primers. Reactions were done using a CFX96 Touch Bio-Rad Real-Time PCR System (Bio-Rad). The PCR conditions were 50° C. for 2 minutes, 95° C. for 2 minutes (initial denaturation) followed by 40 cycles of amplification (95° C. for 15 seconds, 60° C. for 60 seconds), followed by generation of a dissociation curve. At least, three technical replicates were performed for each of the two or three biological replicates. The transcript levels of defense response genes in *Arabidopsis* are shown as fold change relative to mock-treated plants. The relative fold change was calculated according to the 2-ΔΔCt method (Manosalva, et al. (2015) Nat. Commun. 6:7795; Floss, et al. (2013) Proc. Natl. Acad. Sci. 110:E5025-34). Ubiquitin was used as an endogenous reference gene. The paired t-test with an a level of 0.05 was used to compare transcript level in the ascr #18-treated versus the mock-treated samples. For the analyses of RNA from roots, *Arabidopsis* roots were collected from 30-40 seedlings and pooled in one tube. Strand-specific RNA-seq libraries were constructed using a described protocol (Zhong et al. (2011) 2011(8):940-9) and sequenced on the Illumina® NextSeq® 500 platform using 3' single-end sequencing.

Example 1

Plants Metabolize the Pathogen Produced Compound Ascr #18 into a Blend of Chain Shortened Ascarosides (Metabolites)

The following example demonstrates that the targets of pathogens (in this case plants) metabolize pathogen-produced compounds to form metabolites.

Figure 1D:
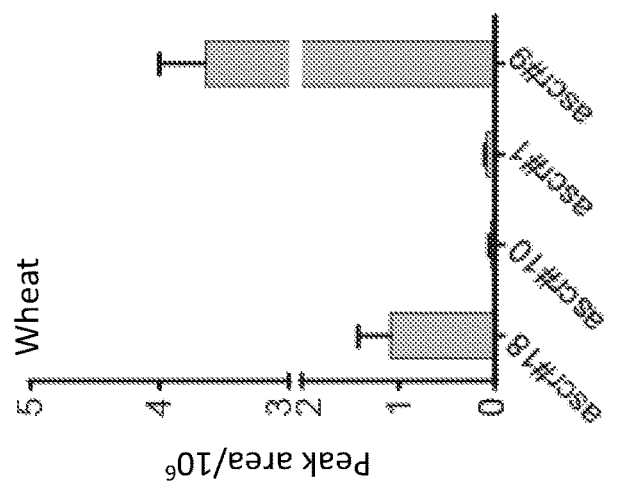
FIG. 1D provides graphs of the accumulation of ascarosides in *Arabidopsis*, tomato, and wheat roots treated with 1 µM ascr #18 for 24 hours. Abundances of ascarosides are shown as the peak area, as measured in LC-MS. Data are averages±SEM (n=5).
Figure 1D:
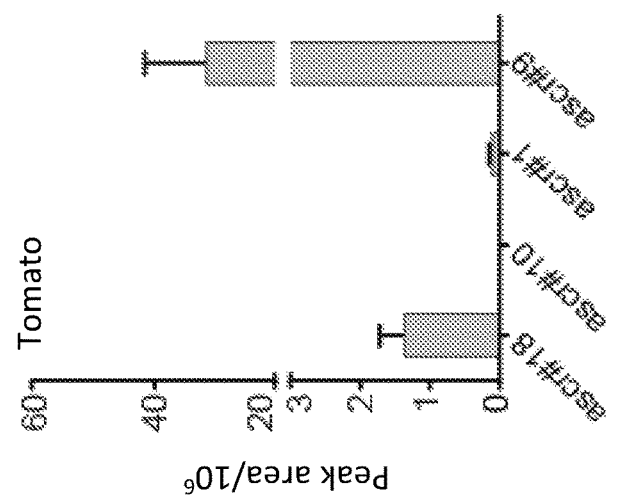
Figure 1D:
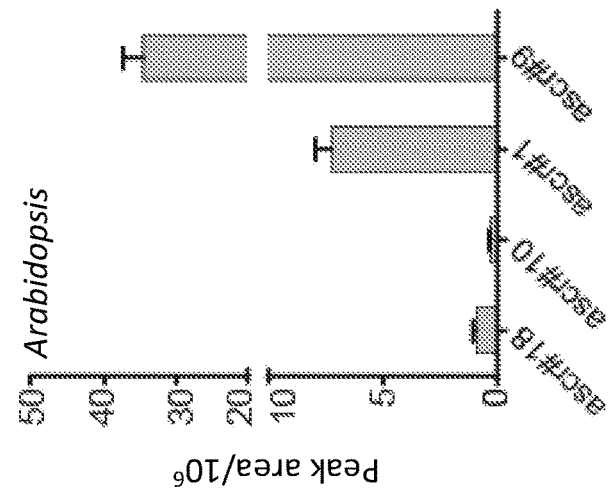
Figure 1E:
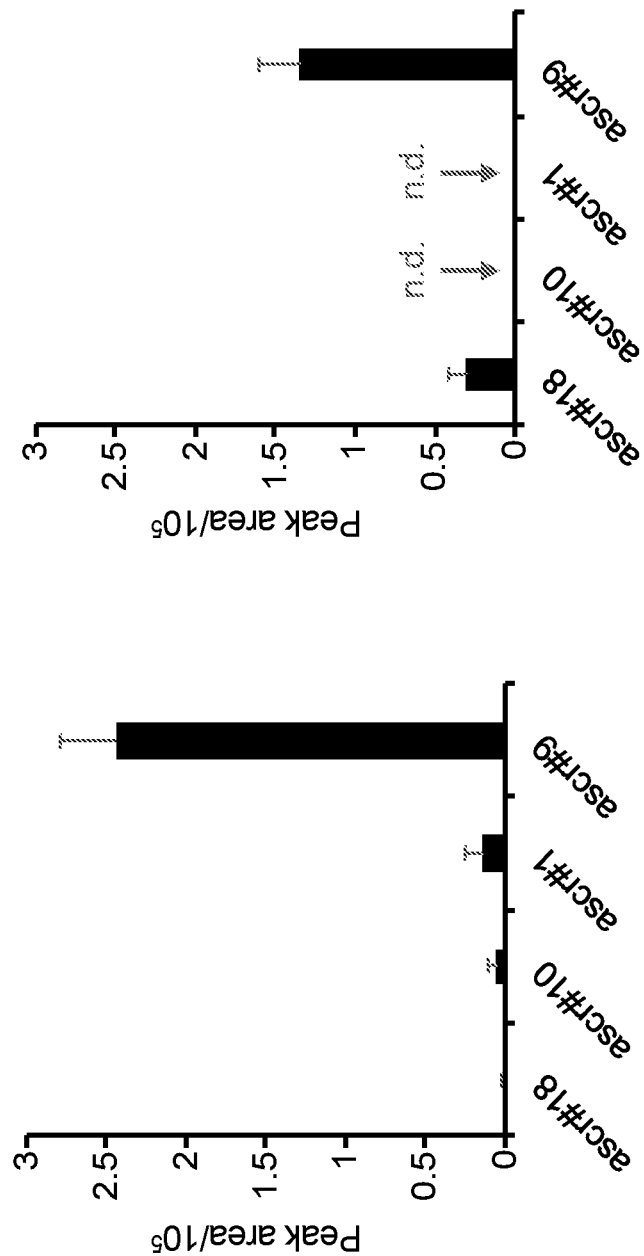
FIG. 1E provides graphs of the accumulation of ascarosides in tomato (left) and wheat (right) roots treated with 10 and 50 nM ascr #18 for 24 hours, respectively. Abundances of ascarosides are shown as the peak area, as measured by LC-MS. Data are averages±SEM (n=5), n.d.=not detected.
Figure 2A:
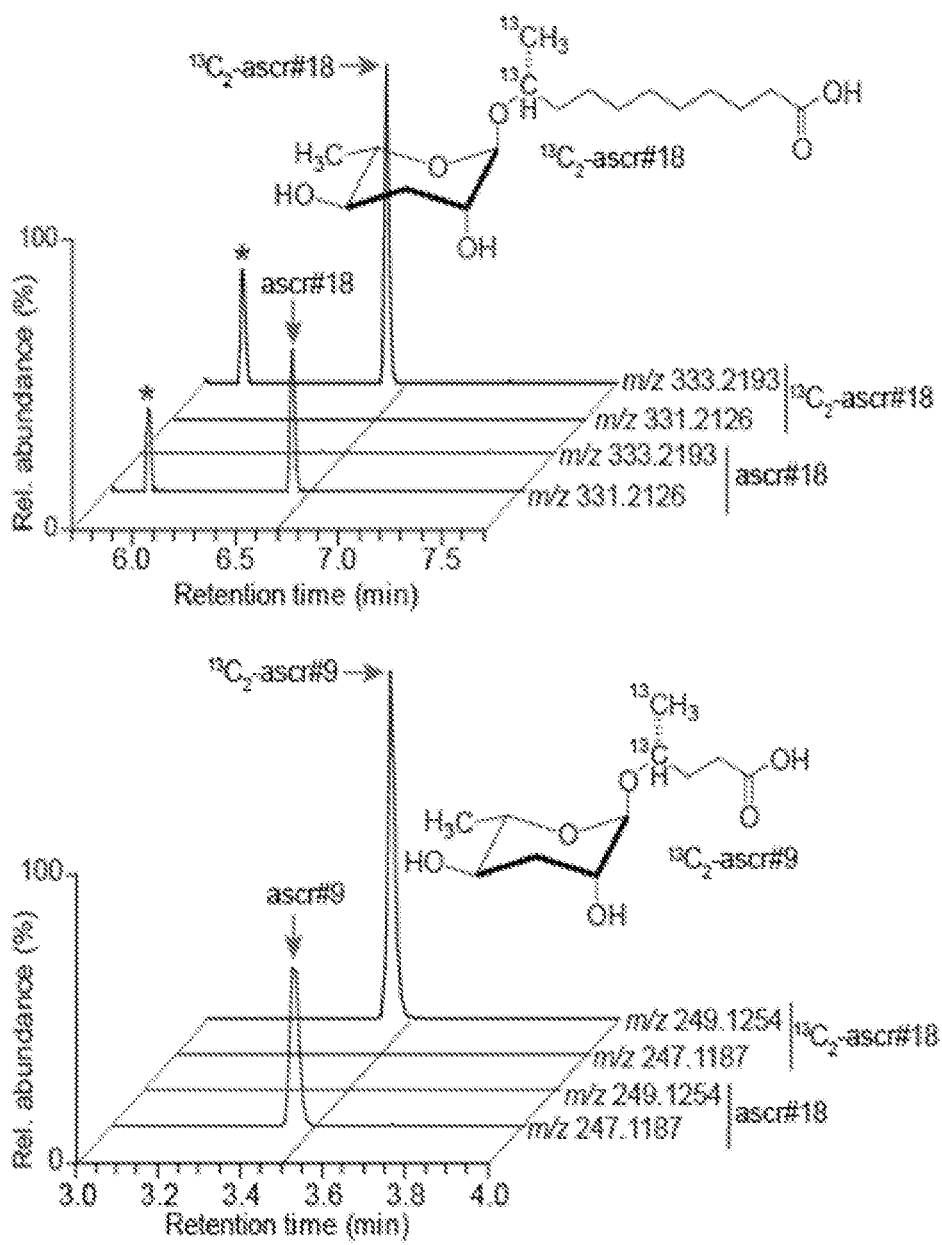
FIG. 2A provides LC-MS analysis of tomato roots treated with ascr #18 or $^{13}C_2$-labeled ascr #18. Plants treated with $^{13}C_2$-labeled ascr #18 show peaks at 333.21932 and 249.12542, representing [M-H]⁻ of $^{13}C_2$-ascr #18 and $^{13}C_2$-ascr #9, but not at 331.21261 and 247.11871, which correspond to [M-H]⁻ of ascr #18 and ascr #9, and vice versa. Structures of ascr #18 and ascr #9 indicating the positions of the $^{13}C_2$-label are shown above ion chromatograms. Peaks marked with an asterisk represent unrelated peaks.

To test whether plants, the target organisms of plant pathogenic nematodes metabolize the pathogen-produced compound ascr #18, comparative metabolomics was employed based on high-resolution LC-MS analyses of ascr #18-treated plant tissues. Dicotyledon tomato and *Arabidopsis* and monocotyledon wheat plants were grown under sterile conditions. Since plants would naturally encounter the pathogenic nematodes via their roots, the roots of these plants were soaked for 24 hours in aqueous ≤0.1% ethanol-containing solutions either with the pathogen-produced compound ascr #18 or without it (mock). Subsequently, root tissue was harvested, extracted and analyzed by LC-MS. To compare datasets from mock- and ascr #18-treated plants, the XCMS comparative metabolomics software package was employed (Tautenhahn, et al. (2012) Anal. Chem. 84(11):5035-9), focusing on peaks that were entirely absent in mock-treated plants and thus could represent ascr #18-derived metabolites. The software-generated lists of differential features were then manually curated to remove false positives as well as isotope peaks and mass spectrometric adducts. For all three plant species, this analysis revealed the presence of ascr #18 in ascr #18-treated but not in mock-treated plants (FIGS. 1C, 1D). In addition, in all three species, a series of additional peaks were found that were present only in ascr #18-treated plants (FIGS. 1C-1E). By comparing molecular ion weights, MS/MS spectra, and retention times with those of known ascarosides (Artyukhin, et al. (2018) J. Am. Chem. Soc. 140(8):2841-2852; Von Reuss, et al. (2012) J. Am. Chem. Soc. 134:1817-1824), it was determined that these additional peaks represent metabolites produced by the target organism from the pathogen-produced compound. The metabolites in this case were found to be ascarosides with shorter side chains, specifically ascr #10, ascr #1, and ascr #9. In all three plant species, ascr #9 was the most abundant differential metabolite (FIG. 1D, 1E). These results indicated that the pathogen-produced compound ascr #18 is taken up and subsequently metabolized into ascarosides with shorter fatty-acid side chains by both monocots and dicots. To corroborate that the shorter-chained ascarosides are derived from the added ascr #18, the experiments were repeated in tomato using $^{13}C_2$-labeled ascr #18 (FIG. 2A). Tomato plants root-treated with $^{13}C_2$-ascr #18 produced $^{13}C_2$-labeled ascr #9, confirming that the shorter-chained plant-produced ascarosides are metabolites derived from the added pathogen-produced compound ascr #18.

Figure 2B:
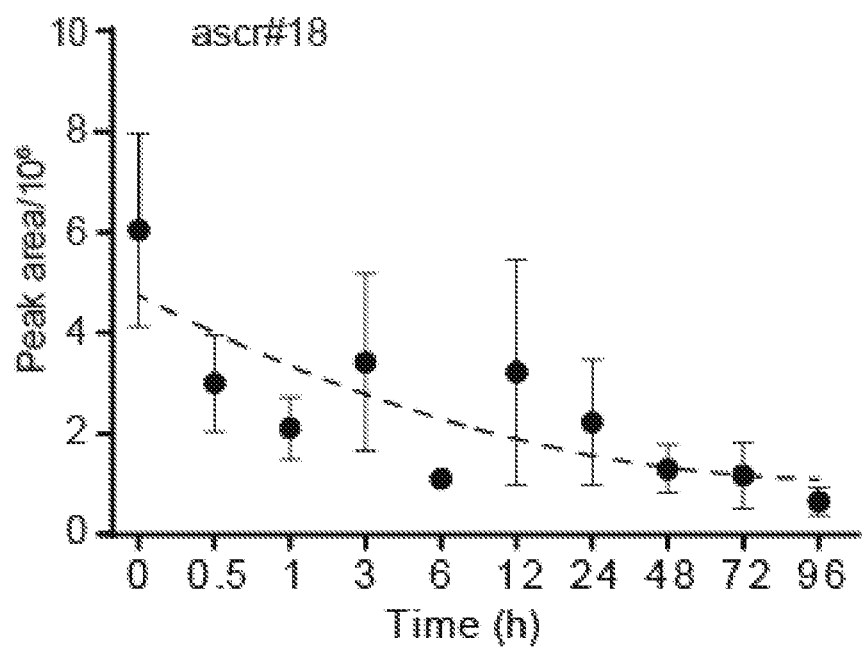
FIGS. 2B and 2C provide graphs showing the relative abundances of ascr #18 and ascr #9, respectively, as measured by LC-MS. Four-week old *Arabidopsis* leaves were infiltrated with 1 μM ascr #18, and leaf tissue were harvested for LC-MS analyses over a period of 96 hours post infiltration of ascr #18. Data are averages±SEM (n=3).
Figure 2C:
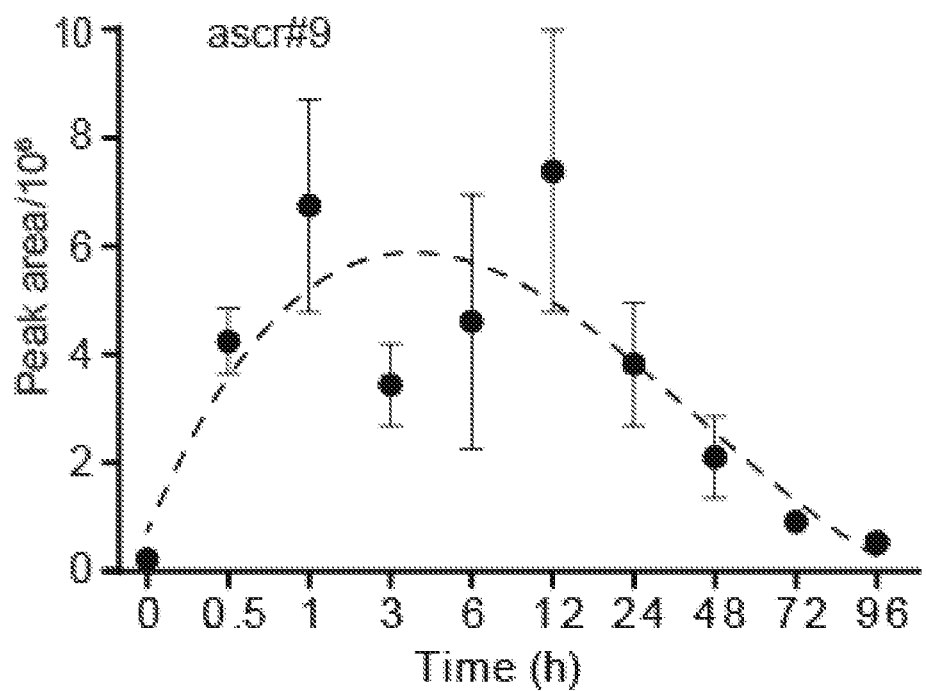
Figure 2D:
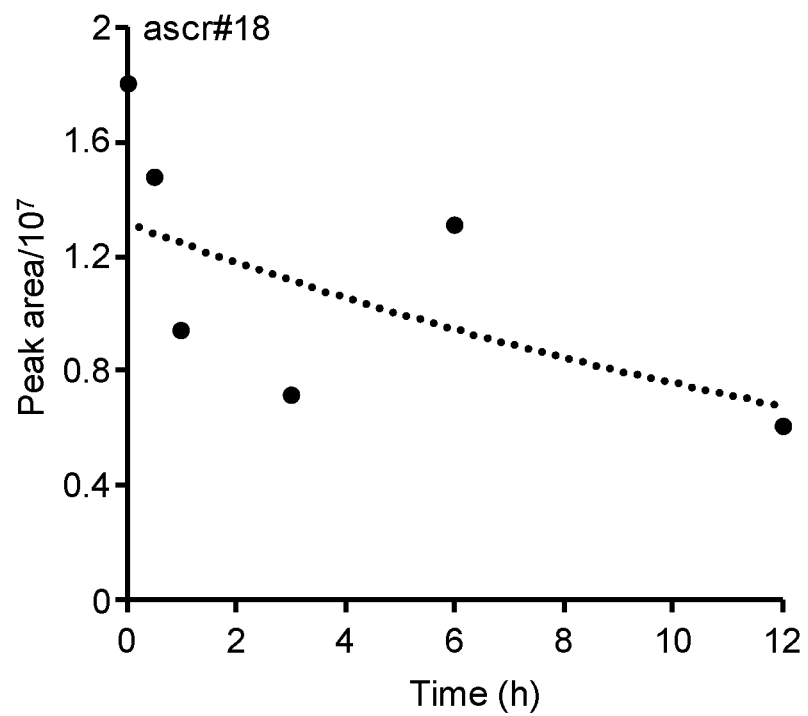
FIG. 2D provides LC-MS analyses of tomato leaves infiltrated with 1 μM ascr #18. Tissues were collected over a 12 hour period. Abundances of ascr #18 and ascr #9 are shown as the peak area, as measured by LC-MS.
Figure 2D:
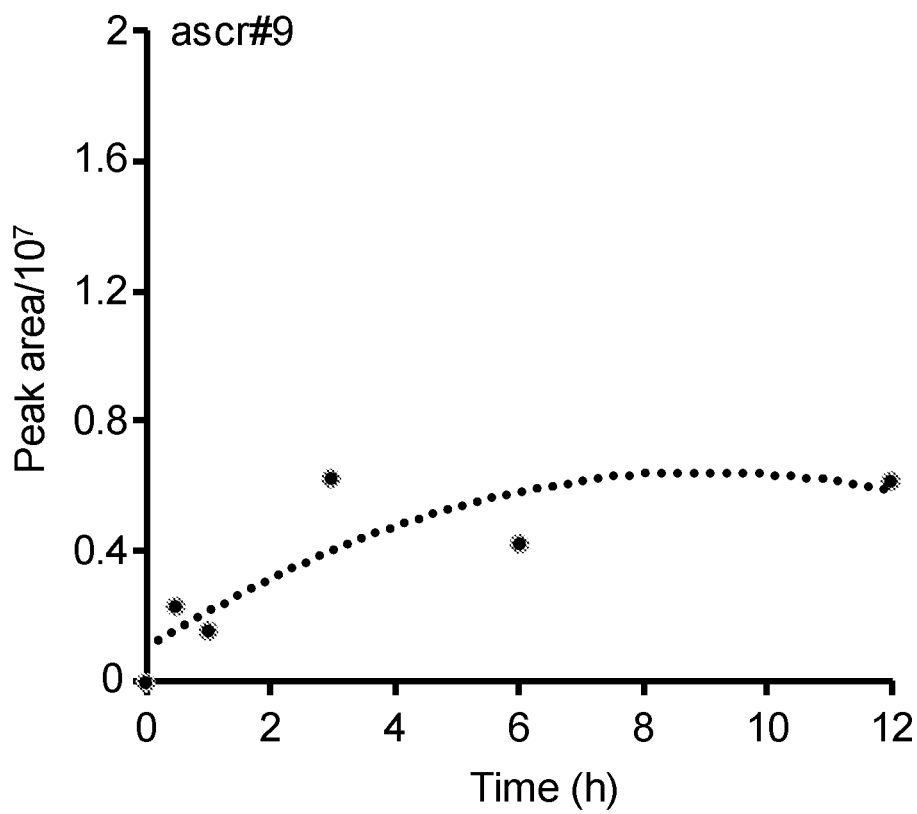

Although the plants used for the ascr #18 experiments were grown under sterile conditions, the possibility that microorganisms, e.g. endophytic microbes associated with the seeds or roots, partake in the metabolism of the ascarosides was considered. To test whether microbes are required for the observed metabolic transformations, leaves of 4-week old *Arabidopsis* plants were directly infiltrated with ascr #18 and leaf tissue was subsequently harvested for analysis by LC-MS as above. Similar to root treatment, the pathogen-produced ascr #18 accumulated and was converted into shorter side-chained ascaroside metabolites in the leaves (FIG. 2B, 2C). About 50% of ascr #18 was metabolized during the first 12 hours, during which time concomitant accumulation of ascr #9 was observed. Formation of ascr #9 was also observed in leaves of 4-week old tomato plants infiltrated with ascr #18 (FIG. 2D). Interestingly, ascr #9 concentrations peaked during the first 12 hours post-infiltration in *Arabidopsis* and subsequently declined to very low levels at 96 hours, indicating that ascr #9 was metabolized further or transported to other tissues in plants (FIG. 2C). Taken together, these experiments demonstrate uptake of ascr #18 and conversion into ascarosides with a shorter side chain, predominately ascr #9, in both monocots and dicots.

Plants Metabolize Ascr #18 Via Peroxisomal β-Oxidation

Figure 3A:
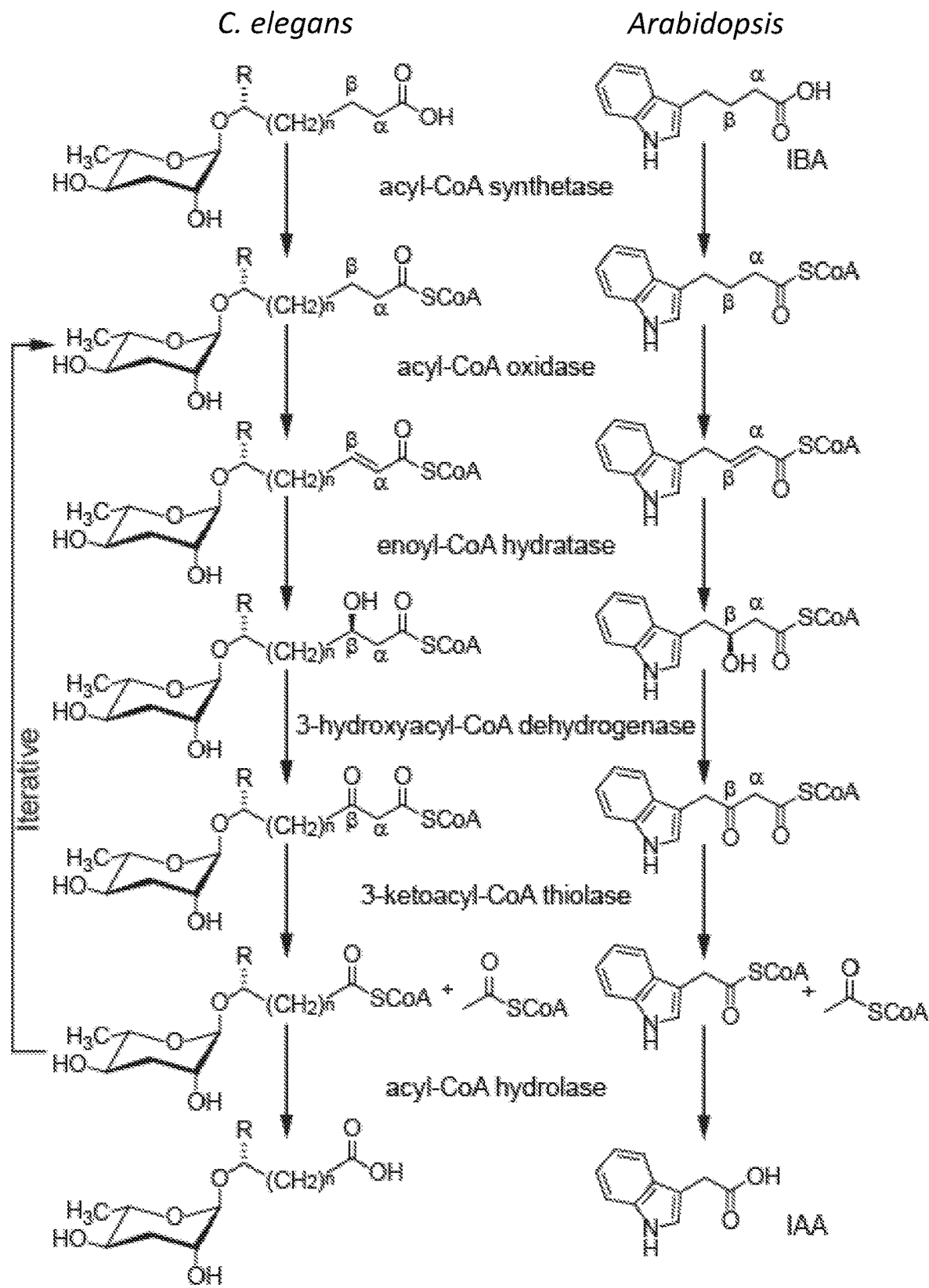
FIG. 3A provides a comparison of peroxisomal β-oxidation (pβo) pathways and associated enzymes involved in the conversion of indole-3-butyric acid (IBA)-to-indole acetic acid (IAA) in *Arabidopsis* and ascaroside biosynthesis in *C. elegans*.

Inspection of the structures of the identified ascr #18-derived metabolites revealed that their side chains are two, four, and six carbons shorter than the side chain of ascr #18 (FIG. 1C). This observation indicated that these compounds may be derived from ascr #18 via β-oxidation. Mitochondrial and peroxisomal β-oxidation are highly conserved metabolic pathways that iteratively shorten straight-chain fatty acids in two-carbon increments. The inventors thus believe the observed metabolism of the pathogen-produced compound ascr #18 is likely representative of other examples of organisms targeted by pathogens taking up and metabolizing pathogen-produced compounds and that beta oxidation is a widespread mechanism by which such metabolism proceeds. Given that fatty acid degradation in plants mostly occurs via the β-oxidation pathway in the peroxisomes (Poirier, et al. (2006) Biochimica et Biophysica Acta—Molecular Cell Research 1763:1413-1426), it was hypothesized that metabolism of ascr #18 in plants may also proceed via pβo. Plant pβo has been extensively characterized genetically and plays an important role in the biosynthesis of signaling molecules. For example, pβo contributes to the biosynthesis of jasmonic acid and auxin (Strader, et al. (2011) Plant Cell 23:984-999). A general scheme comparing the pβo pathways in *Arabidopsis* and *C. elegans* is shown in FIG. 3A.

Figure 3B:
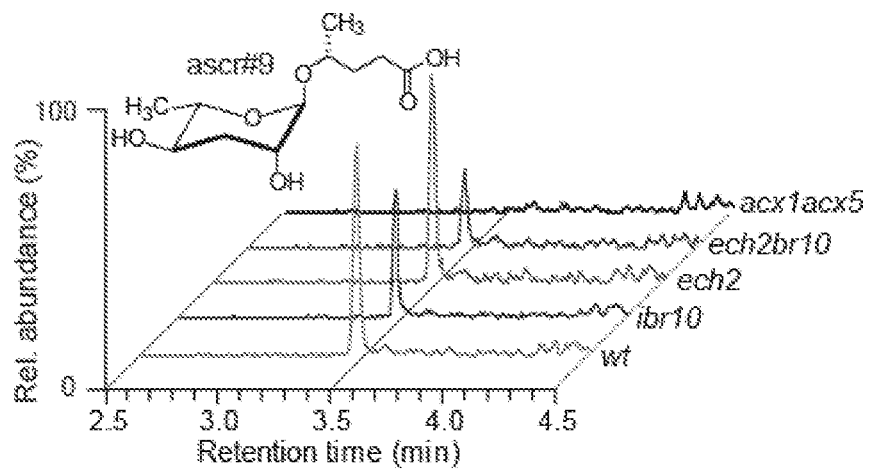
FIG. 3B provides LC-MS analysis of *Arabidopsis* seedlings treated with 1 μM ascr #18 for 24 hours before sample extraction, comparing ascr #9 production in wildtype and ibr10, ech2, ech2ibr10, or acxlacx5 mutants.
Figure 3C:
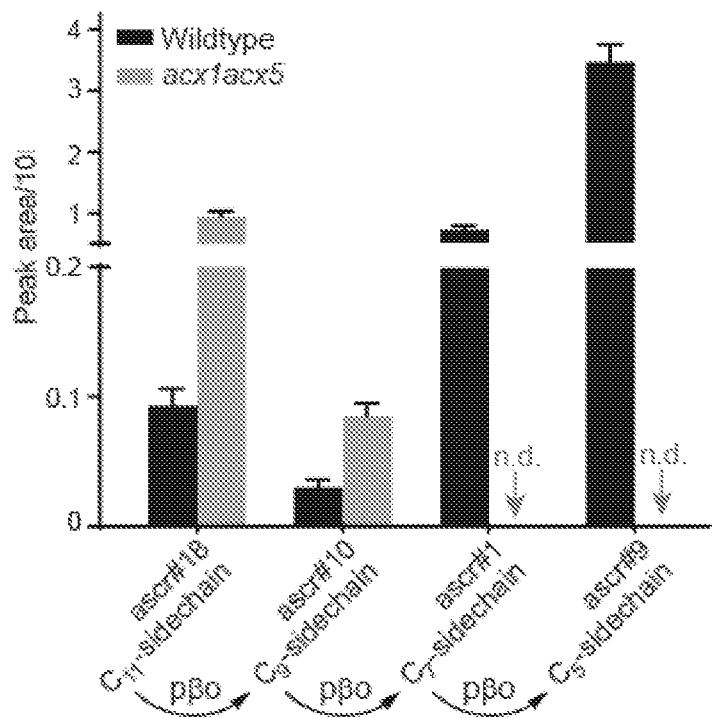
FIG. 3C provides a comparison of ascaroside abundances in *Arabidopsis* wildtype and acxlacx5 roots treated with 1 μM ascr #18. Data are averages±SEM (n=5); n.d.=not detected.
Figure 3D:
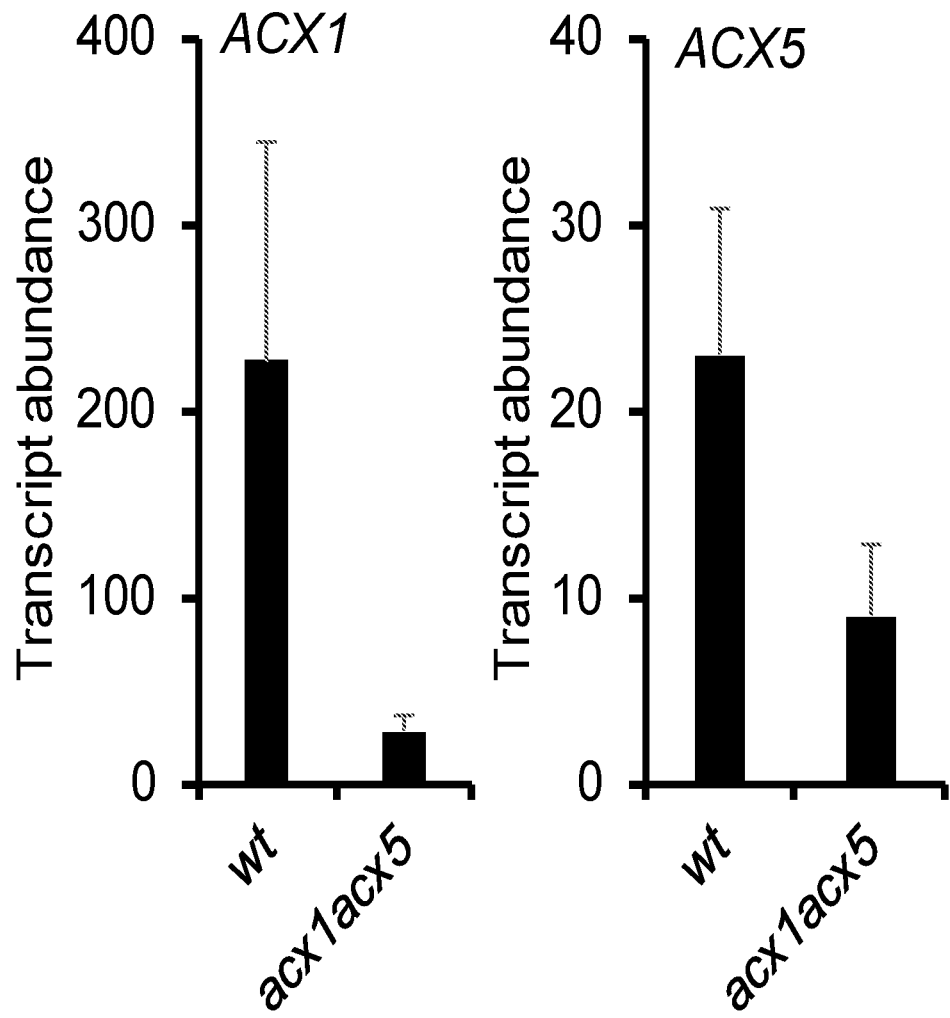
FIG. 3D provides RNAseq analysis of ten day-old *Arabidopsis* wildtype and acxlacx5 mutant roots, plotted as transcript abundance. Data are averages±s.d (n=6).

To test whether ascr #18 is metabolized via pβo in plants, *Arabidopsis* mutants impaired in key enzymes of this pathway were analyzed (FIG. 3B). It was found that metabolism of ascr #18 into shorter-chained ascarosides was dramatically reduced in an *Arabidopsis* mutant defective in two of the six annotated acyl-CoA oxidases, acx1 and acx5 (Adham, et al. (2005) Plant J. 41:859-874). Partial abolishment of ACX1 and ACX5 transcription in the acx1acx5 mutant has been demonstrated (Adham, et al. (2005) Plant J. 41:859-874) and was confirmed by RNAseq analysis (FIG. 3D). In contrast, two other putative pβo genes, ibr10 and ech2, a putative enoyl-CoA hydratases (Strader, et al. (2011) Plant Cell 23:984-999; Adham, et al. (2005) Plant J. 41:859-874; Zolman, et al. (2008) Genetics 180(1):237-51), are not required for ascr #18 metabolism in *Arabidopsis*. ACXs participate in the second step of pβo by introducing α,β-unsaturation in the side-chain (Von Reuss, et al. (2012) J. Am. Chem. Soc. 134:1817-1824; Strader, et al. (2011) Plant Cell 23:984-999). Detailed metabolomic comparison of ascr #18-treated wildtype and acx1acx5 plants revealed that the mutant accumulated elevated levels of ascr #18 (11-carbon side chain) as well as smaller amounts of ascr #10 (9-carbon side chain) whereas ascr #1 and ascr #9 (7- and 5-carbon chains, respectively) were not detected (FIG. 3C). These observations indicate that ascr #18 metabolism in plants into shorter-chained ascarosides proceeds via pβo, and that ACX1 and/or ACX5 are strictly required for chain shortening of ascr #10, whereas the first chain-shortening step from ascr #18 to ascr #10 may involve additional acyl-CoA oxidases.

Example 2

Enhanced Resistance to Nematodes, but not Bacteria, Requires Ascr #18 Metabolism As described hereinabove, in certain embodiments, the formulations and methods of the present invention protect target organisms not only against the pathogen that produces the pathogen-produced compound, but may additionally afford the organism protection against other pests, parasites, or pathogens that do not produce the compound. The following example demonstrates that in the case of plants, protection against pathogenic nematodes according to embodiments of the present invention has the potential to additionally protect the plant against other non-nematode pathogens. The following example demonstrates an example of this effect wherein the resistance of the organism (in this case monocot or dicot plants) to the pathogen that excretes the pathogen-produced compound (in this case, pathogenic nematodes that excrete ascr #18) is dependent on the metabolism of the compound by the plant but the protection of the plant against other pathogens (in this case bacteria) does not require the pathogen-produced compound to undergo metabolism. These experiments demonstrate that a commercially desirable dual effect can be obtained by the methods herein and indicate that methods and formulations of the present invention may unexpectedly act by multiple modes of action.

Given the rapid conversion of ascr #18 into shorter-chained ascarosides via pβo, the inventors investigated whether metabolism of the pathogen-produced compound ascr #18 produced by plant pathogenic nematodes is required for the activation of plant defense responses and resistance to other non-nematode pathogens. Ascr #18 has been shown to enhance resistance of monocot and dicot plants to a wide range of pathogens, including bacteria, viruses, fungi, oomycetes, and nematodes (Manosalva, et al. (2015) Nat. Commun. 6:7795). To test whether ascaroside metabolism plays a role in ascr #18-mediated enhanced resistance to a bacterial pathogen, the effect of ascr #18 treatment on infection with *Pseudomonas syringae* DC3000 was evaluated in the acx1acx5 mutant and wildtype *Arabidopsis*. Pretreatment with 1 µM ascr #18 for 24 hours prior to infection with *P. syringae* provided comparable levels of protection in acx1acx5 and wildtype (FIG. 4A, 4B), indicating that metabolism of ascr #18 via acx1acx5 is not required for enhanced resistance against this bacterial pathogen.

To assess whether plant metabolism of ascr #18 contributes to defense against nematodes, the effect of ascr #18 treatment was compared on infection of wildtype and the acx1acx5 mutant with root-knot nematode (*Meloidogyne incognita*). It was found that, whereas pretreatment of roots with 10 nM or 50 nM ascr #18 for 48 hours prior to inoculation provided significant protection against the ascr #18-producing pathogen in wildtype plants, ascr #18 treatment had no effect in the acx1acx5 mutant (FIG. 4A, 4C).

Figure 4A:
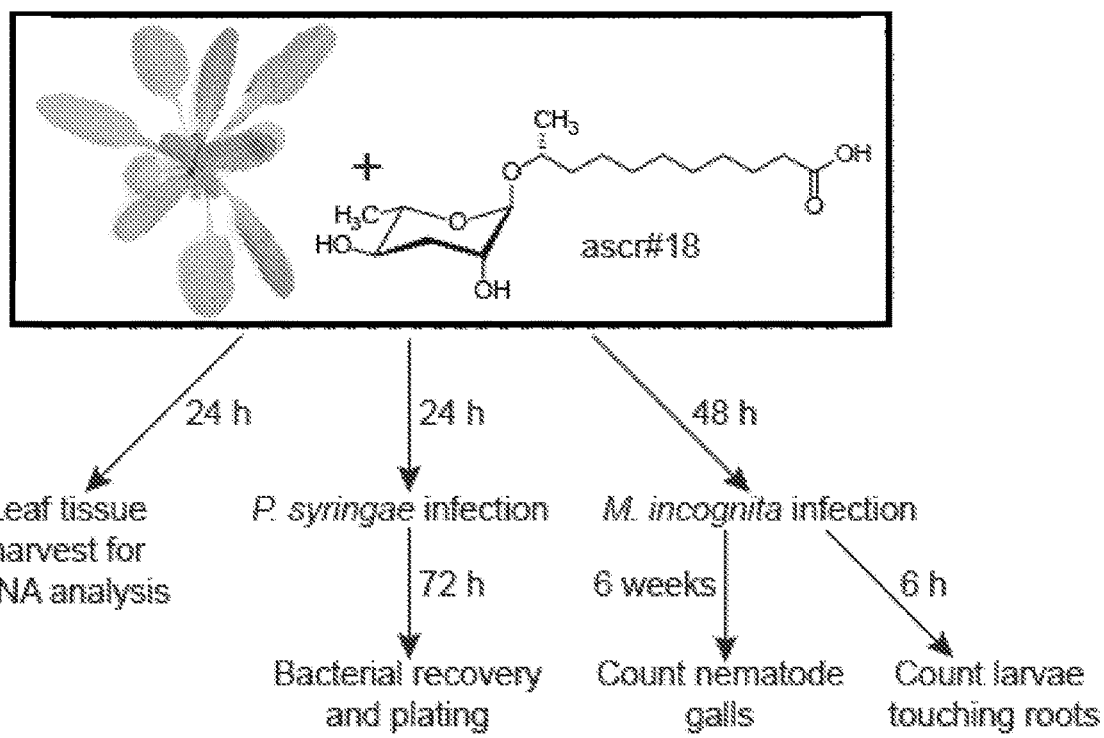
FIG. 4A provides a schematic of the experimental designs for assessing activation of defense pathways and resistance to nematodes and bacteria.
Figure 4B:
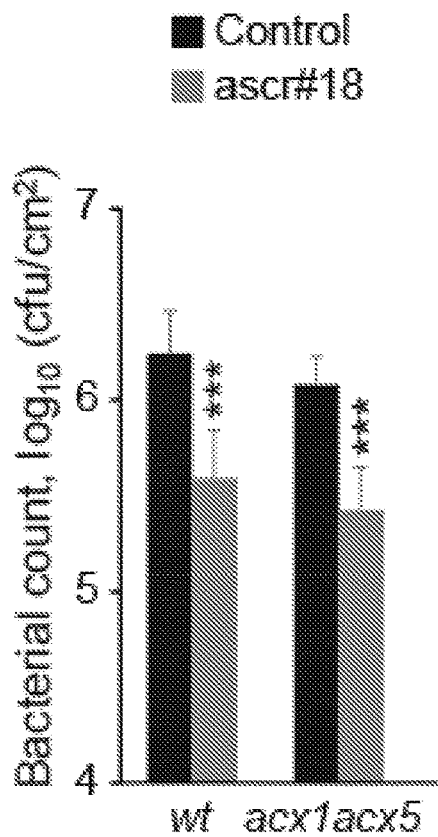
FIG. 4B shows enhanced resistance to virulent *P. syringae* pv. tomato (Pst) DC3000 does not require acxlacx5. Bacterial growth was assayed 3 days post inoculation. Data are averages±s.d. (n=17).
Figure 4C:
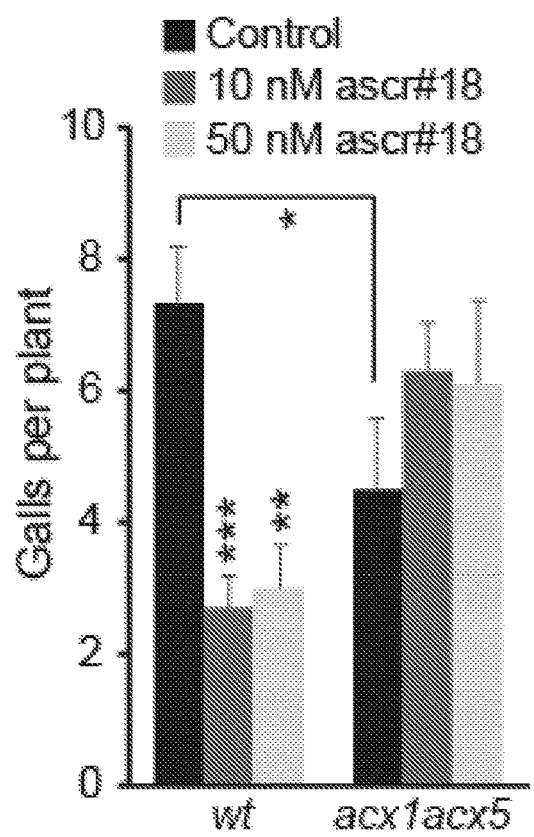
FIG. 4C shows that ascr #18 increases resistance of *Arabidopsis* wildtype, but not acxlacx5 mutants, to plant parasitic nematodes (*M. incognita*). *Arabidopsis* seedlings were treated with buffer or the indicated concentrations of ascr #18 for 48 hours before inoculation with approximately 300 freshly hatched *M. incognita* J2 larvae. The numbers of root galls of infected plants were counted 6 weeks post inoculation. Data are averages±s.d. (n≥15).
Figure 4D:
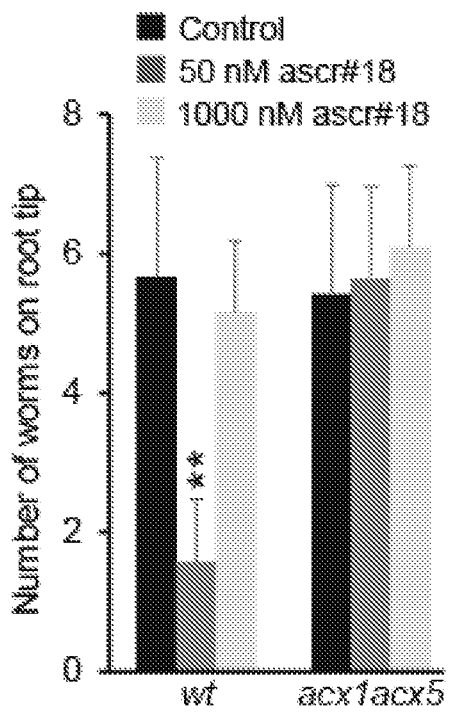
FIGS. 4D and 4E show that ascr #18 treatment of *Arabidopsis* wildtype, but not acxlacx5 mutants results in deterrence of *M. incognita* J2 larvae resistance. *Arabidopsis* seedlings were treated with the indicated concentrations of ascr #18 for 48 hours before transfer into 12-well plates containing Pluronic® F-127 gel with ~200 freshly hatched *M. incognita* J2 larvae. Larvae touching root tips (FIG. 4D) or the whole area of roots (FIG. 4E) were counted at 6 hours post seedling transfer. Data are average±s.d. (n=12).
Figure 4E:
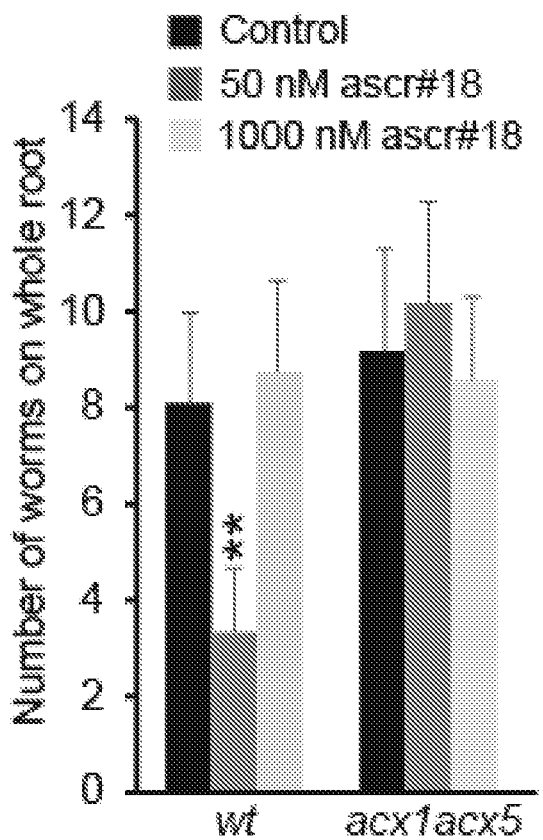

In a second experiment, wildtype and acx1acx5 were treated with ascr #18 for 48 hours prior to moving seedlings to a PF-127 gel containing approximately 200 *M. incognita* second-stage larvae (J2) (FIG. 4A, 4D, 4E). J2 larvae touching the roots were counted at 6 hours post seedling transfer. In response to pretreatment with ascr #18 at 50 nM, numbers of J2 larvae touching the root tips or whole root area were significantly reduced in wildtype, but not in acxlacx5. A second, much higher ascr #18 concentration (1 µM) did not significantly affect M. incognita behavior in either wildtype or mutant. Taken together, these results indicate that ascr #18 metabolism is required for the enhanced resistance of ascr #18-treated plants to nematode infection, whereas ascr #18 metabolism is not necessary to afford resistance to bacteria.

These findings confirm two unexpected results: first that a signaling compound produced by a pathogen (the pathogenic nematode) is taken up and metabolized by the target of that pathogen (the plant) to create a metabolite that effectively deters the pathogen from harming the target; and secondly that the presence of the pathogen-produced compound also has utility in protecting the target from species other than the pathogen producing the compound, but that metabolism of the pathogen-produced compound is not required to elicit the effect against these other species. This is highly unexpected and confirms the concept that the metabolites generated by the target organism from the pathogen-produced compounds are especially effective in protecting the target against the particular pathogen responsible for producing the compound that is metabolized, but this metabolism is not required to elicit protection against other pathogens that are not responsible for making the pathogen-produced compound.

Activation of Defense Signaling Pathways is Independent of Ascr #18 Metabolism

Figure 4F:
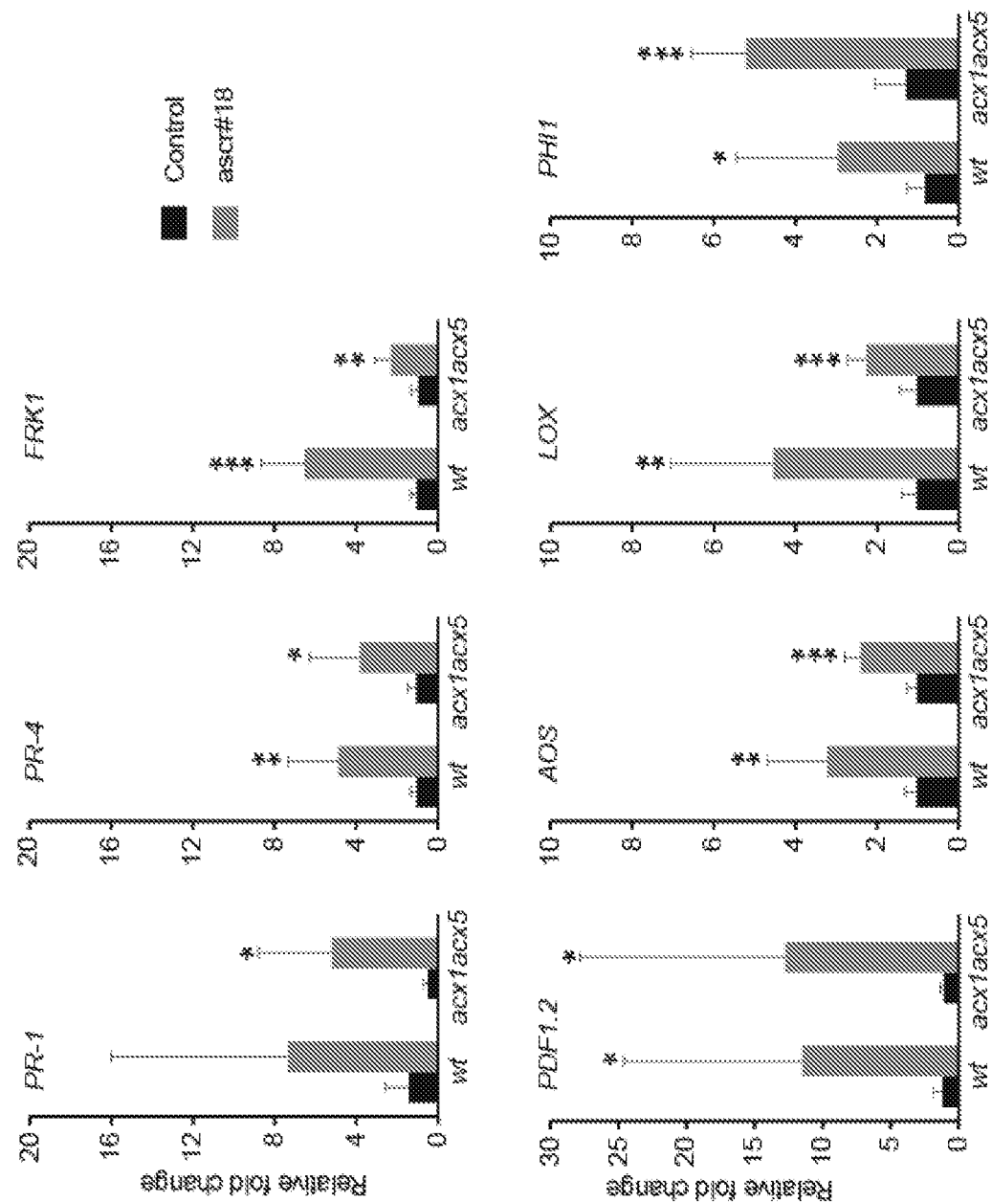
FIG. 4F shows induction of defense-response genes in *Arabidopsis* leaves 24 hours after root treatment with 1 μM ascr #18. Transcript levels were determined by qRT-PCR and plotted as relative fold-change compared to mock treated plants. Data are averages±s.d (n≥6). *P≤0.05; P≤0.005; *P≤0.0005; two-tailed t-test.

Next, it was determined whether differences in activation of defense signaling in wildtype and acxlacx5 plants underlie the observed differences in resistance to nematodes. Ascr #18 treatment results in activation of conserved defense signaling pathways in monocots and dicots, including mitogen-activated protein kinase (MAPK) signaling and the jasmonic acid (SA) and salicylic acid (SA) signaling pathways (Manosalva, et al. (2015) Nat. Commun. 6:7795). To assess whether ascr #18 metabolism via pβo is required for activation of these defense signaling pathways, expression of selected marker genes was compared in leaves of ascr #18-treated wildtype and acxlacx5 plants (FIG. 4F, Table 1). Treatment with ascr #18 induced components of jasmonic acid signaling (Plant Defensin 1.2 (PDF1.2), Allene Oxidase Synthase (AOS), and Lipooxygenase 2 (LOX2)) and salicylic acid signaling (Pathogenesis-Related 1 (PR-1) and Pathogenesis Related 4 (PR-4)) to similar extents in wildtype and the acxlacx5, although induction of the MAPK-related Flg22-Induced Receptor Kinase 1 (FRK1) was slightly weaker in the mutant. These findings indicate that ascr #18 metabolism via pβo is generally not required for activation of canonical defense signaling pathways by ascr #18. The observation that enhanced protection of *Arabidopsis* against *P. syringae* is independent of ascr #18 metabolism is consistent with this result. However, given that enhanced resistance against nematodes does require ascr #18 metabolism, it appears that activation of these canonical defense signaling pathways is not sufficient to explain the observed protection against nematodes in ascr #18-treated wildtype plants.

Example 3

Plant Roots Secrete Ascr #18 Metabolites

Plants secrete a large array of primary and secondary metabolites via their roots, including signaling molecules that facilitate interactions with soil biota (van Dam, et al. (2016) Trends Plant Sci. 21:256-265). Since ascr #18 metabolism is not required for resistance against bacteria or activation of the canonical plant defense signaling pathways, but nonetheless is essential for defense against nematodes, the possibility was considered that ascr #18-derived metabolites are secreted via the roots and thereby affect nematode host finding behavior.

Figure 5A:
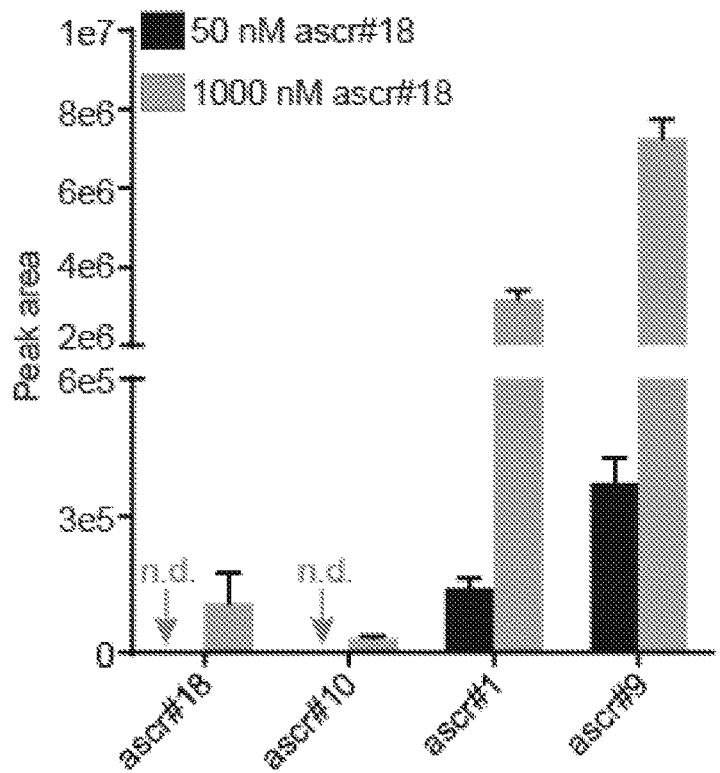
FIG. 5A shows relative abundances of ascarosides in root exudates of *Arabidopsis* treated with 50 nM and 1000 nM ascr #18, as determined LC-MS. Data are average±SEM (n=6), n.d.=not detected.
Figure 5B:
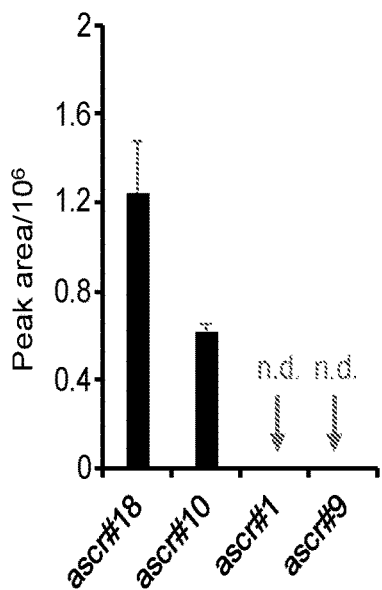
FIG. 5B shows the relative abundances of ascarosides in root exudates of ten-day old *Arabidopsis* acxlacx5 mutant seedlings treated with 10 nM ascr #18 for 6 hours. Exudates from approximately 40 seedlings were collected in distilled water and pooled. Abundances of ascarosides are shown as the peak area, as measured by LC-MS. Data are average±SEM (n=3); n.d.=not detected.
Figure 5C:
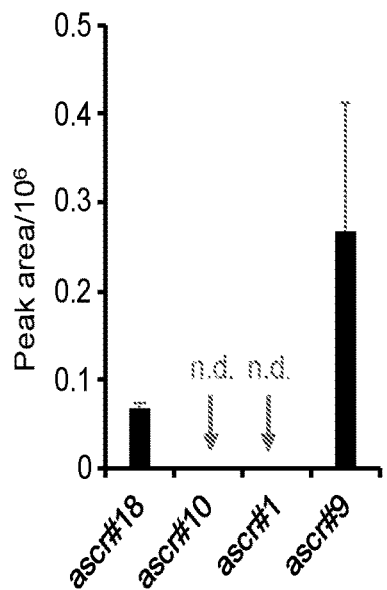
FIGS. 5C and 5D show the relative abundances of ascarosides in root exudates of eight-day old tomato seedlings treated with 10 nM (FIG. 5C) or 1000 nM (FIG. 5D) ascr #18 for 6 hours. Exudates from approximately 10 seedlings were collected in distilled water and pooled. Abundances of ascarosides are shown as the peak area, as measured by LC-MS. Data are average±SEM (n=3); n.d.=not detected.
Figure 5D:
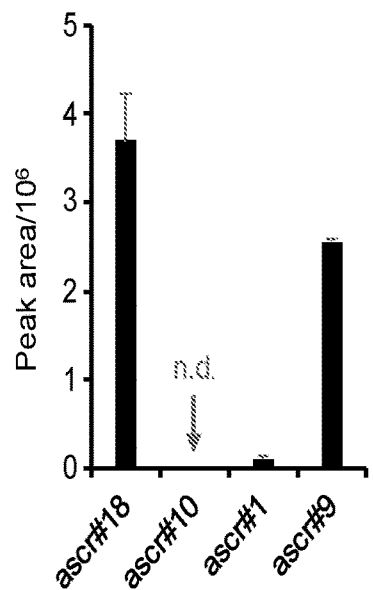
Figure 5E:
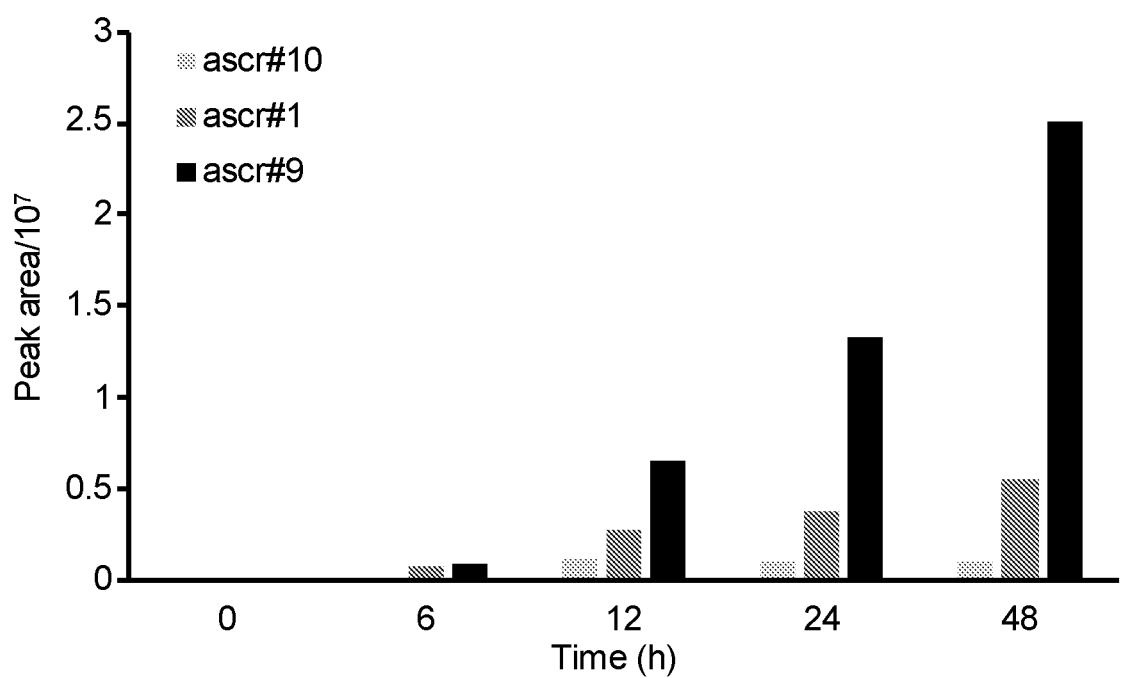
FIG. 5E provides the relative abundances of ascr #10, ascr #1, and ascr #9 in the growth media of eight-day old tomato seedlings supplemented with 1 μM ascr #18. Ten-gram media samples were collected at different time points over a 48 hour period for metabolome extraction. Abundances of ascarosides are shown as the peak area, as measured by LC-MS.

To test this possibility, root-secreted metabolites of ascr #18- and mock-treated *Arabidopsis* were compared (FIG. 5A). For this experiment, 10-day old *Arabidopsis* seedlings were treated in growth media supplemented with ascr #18 for 6 hours prior to collection of exudates from roots submerged in water. HRLC-MS-based comparative metabolomic analyses revealed secretion of all of the identified ascr #18 metabolites, including ascr #10, ascr #1, and ascr #9, in ascr #18-treated wildtype. Consistent with the above results, only ascr #10 was detected in acxlacx5 in addition to larger amounts of residual ascr #18 than in wildtype (FIG. 5B). Analogous results were obtained in experiments with tomato roots (FIG. 5C, 5D). HRLC-MS analysis of growth media showed a steady buildup of short-chained ascarosides over a period of 48 hours post treatment, indicating constant uptake, conversion, and excretion of ascarosides through the root (FIG. 5E). In both tomato and *Arabidopsis*, ascr #9 was the most abundant root-excreted ascr #18 metabolite, whereas ascr #10 was least abundant.

Example 4

Plant-Derived Ascaroside Blends Deter Plant-Parasitic Nematodes

This example demonstrates an embodiment of the present invention where the target organism of a pathogen is treated with a formulated blend of a compound produced by that pathogen in combination with a metabolite produced by the target organism from the pathogen-produced compound.

Figure 6C:
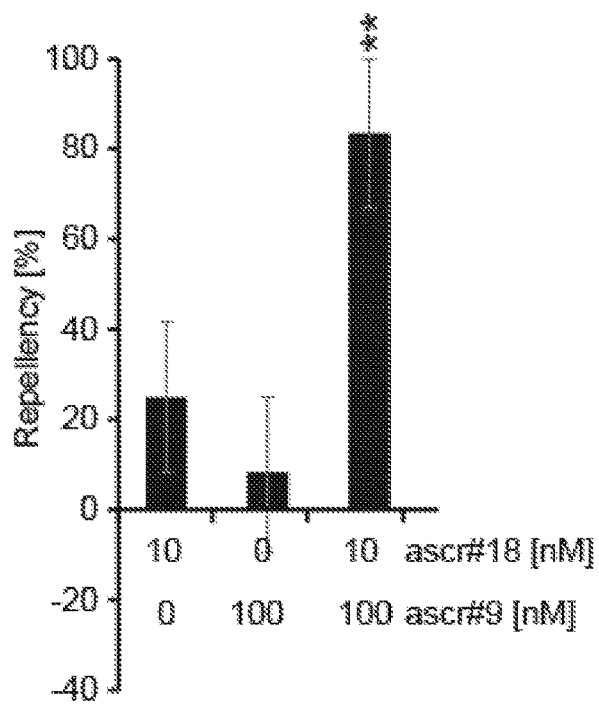
FIG. 6D provides the attraction index for different concentrations of ascr #18, ascr #9, or ascr #18/ascr #9 mixtures measured using the layout shown in FIG. 6C. Data are averages±SEM (n=12), P≤0.002; two-tailed t-test.
Figure 6D:
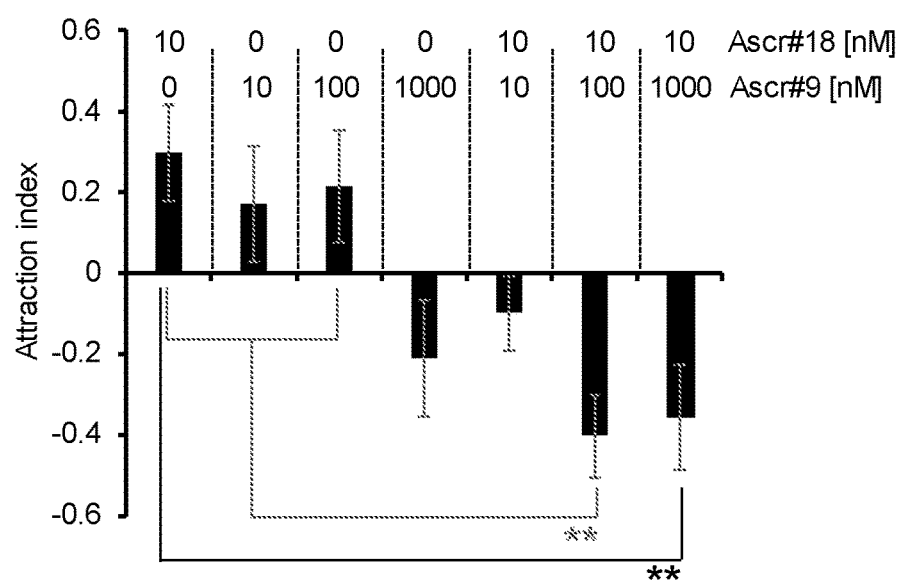
Figure 7:
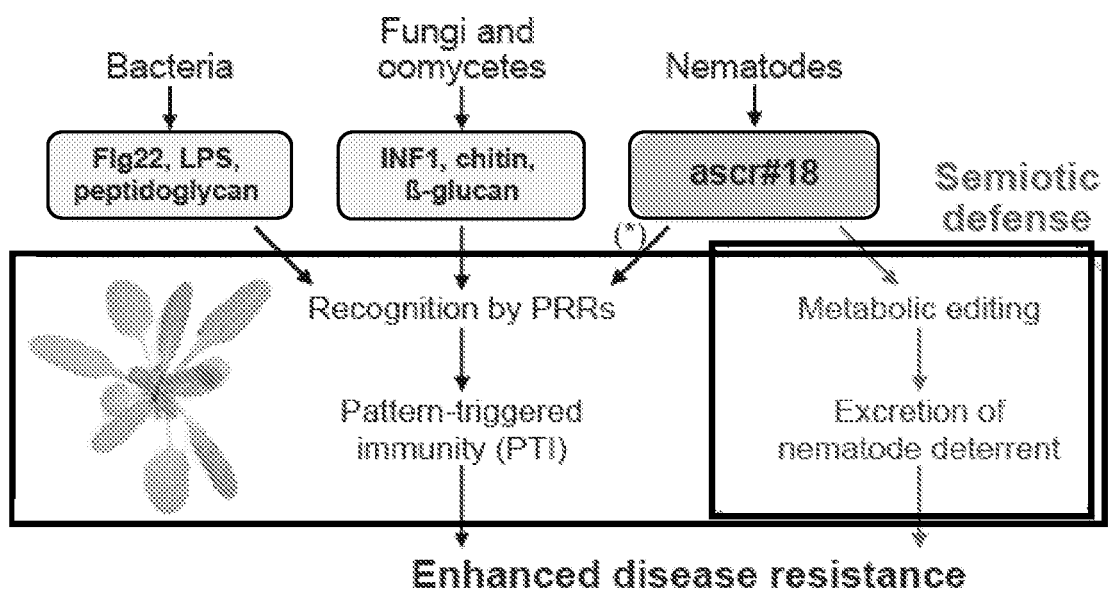
FIG. 7 provides a schematic of the editing of ascr #18 and generation of repellent signals which act in parallel with conventional innate immune responses in plants. Plants detect PAMPs such as flg22, lipopolysaccharide (LPS), and peptidoglycan derived from bacteria, infestin 1 (INFO, chitin, and β-glucan derived from fungi/oomycete, and ascr #18 derived from nematodes via cell-surface localized PRRs to induce conventional PTI. A parallel "semiotic defense" depends on metabolic editing of nematode-derived ascr #18 by the plant to generate a cocktail of ascarosides pheromones that acts as a repellent of parasitic nematodes.

The most abundant ascr #18 metabolite, ascr #9, can mediate dispersal behavior in entomopathogenic nematode species (Kaplan, et al. (2012) PLoS One 7(6):e38735), which are phylogenetically related to *Meloidogyne* spp. (Blaxter, et al. (2015) Parasitology 142(Suppl. 1):S26-S39; Dorris, et al. (1999) Parasitology Today 15(5):188-93; Blaxter, et al. (1998) Nature 392:71-75). Therefore, the secretion of ascr #9 may play a role in mediating plant-nematode interactions. However, treatment of either wildtype or acxlacx5 with ascr #9 for 48 hours before moving seedlings to PF-127 gel containing M. incognita J2 larvae did not significantly reduce infection (FIG. 6A), indicating a blend of ascarosides, not just one compound, may be responsible for the observed suppression of nematode migration towards roots. Therefore, a series of combinations of ascr #18 and its most abundant metabolite, ascr #9, were tested in a quantitative chemotaxis population assay (Zhou, et al. (2017) Genetics 206:1469-1478) (FIG. 6B). It was found that blends containing a 1:10 ratio of ascr #18 to ascr #9 elicited significant avoidance behavior, whereas blends containing primarily ascr #18 as well as the individual compounds had no significant effect (FIG. 6C, 6D). These surprising results show that a blend of pathogen-produced compound in combination with one or more metabolites of that compound produced by the target of the pathogen are effective in deterring the pathogen, whereas the metabolites alone have little or no effect. The inventors further discovered that the blend of ascr #9 in combination with ascr #18 repels nematodes in the rhizosphere and thereby reduces infection by pathogenic nematodes.

Conversion of ascr #18 into shorter side-chained ascarosides provides the first example in which enzymatic editing of a PAMP molecule in planta is required for PTI. It is demonstrated herein that editing of ascr #18 proceeds via peroxisomal β-oxidation (pβo) in *Arabidopsis* and that a mutant defective in two peroxisomal acyl-CoA oxidases is defective in ascr #18-triggered defense against nematodes. Metabolism of ascr #18 in plants is reminiscent of ascaroside biosynthesis via pβo in *C. elegans* (Von Reuss, et al. (2012) J. Am. Chem. Soc. 134:1817-1824). Pβo is highly conserved in animals and plants and plays a central role in energy metabolism as well as diverse signaling pathways, e.g. by contributing to the biosynthesis of the plant hormones auxin and jasmonic acid (Poirier, et al. (2006) Biochimica et Biophysica Acta—Molecular Cell Research 1763:1413-1426; Strader, et al. (2011) Plant Cell 23:984-999; Adham, et al. (2005) Plant J. 41:859-874). Analogous to pβo in *C. elegans* and other animals, acyl-CoA oxidases (ACX) catalyze the first step of the plant pβo cycle and essentially determine the flux of metabolites through this pathway, although biochemical characterization of pβo in *Arabidopsis* remains incomplete (Poirier, et al. (2006) Biochimica et Biophysica Acta—Molecular Cell Research 1763:1413-1426; Strader, et al. (2011) Plant Cell 23:984-999; Adham, et al. (2005) Plant J. 41:859-874; Zolman, et al. (2008) Genetics 180(1):237-51; Zolman, et al. (2007) Plant Mol. Biol. 64(1-2):59-72; Arent, et al. (2010) J. Biol. Chem. 285(31):24066-77). The *Arabidopsis* genome contains six ACX paralogs, of which four (ACX1-4) have been characterized in greater detail. ACX1 has medium-to-long chain substrate specificity with ACX5 sharing nearly 85% of sequence identity. They are presumed to be functionally similar (Poirier, et al. (2006) Biochimica et Biophysica Acta—Molecular Cell Research 1763:1413-1426; Adham, et al. (2005) Plant J. 41:859-874). The observation that, whereas conversion of ascr #18 into ascr #10 by one round of pβo was only partially affected in acxlacx5, metabolism of ascr #10 into shorter side-chained ascarosides was completely abolished in this mutant, indicates that ACX1 and/or ACX5 are specifically required for the chain-shortening of ascr #10. Rapid metabolism of ascr #18 by plants suggests that evolution of plant pβo may have been shaped in part by selective advantages conferred by the capability to interfere with nematode chemical communication. Notably, ascr #18-mediated resistance to bacterial pathogens remains unaffected in the acxlacx5. Independent of pβo, ascr #18 induces expression of defense genes in roots, and it is possible that induction of innate plant immunity by ascr #18 may also contribute to nematode resistance.

Enzymatic editing by infected plants or animals likely also plays a role in the perception of microbial PAMPs. For example, plant perception of bacterial flagellin via the conserved flg22 epitope is presumed to involve extensive deglycosylation (Taguchi, et al. (2003) Plant Cell Physiol. 44(3):342-349; Takeuchi, et al. (2003) J. Bacteriol. (2003) 185(22):6658-6665), though responsible plant enzymes have not been identified (Mbengue, et al. (2016) Proc. Natl. Acad. Sci. 113:11034-11039; Robatzek, et al. (2006) Genes Dev. 20:537-542).

Example 5

Herein, an example of a synthesis protocol for ascr #18 is provided. The method may be modified to synthesize other ascarosides described herein. For example, the synthesis of ascr #18 metabolites such as ascr #1, ascr #10, and ascr #9 can be performed by replacing 7-bromoheptene in step 1 with a bromo containing compound having the correct number of carbons in the chain for the desired ascaroside.

Synthesis of Ascr #18

Starting materials were synthesized as described in cited references or purchased from Sigma-Aldrich or Acros Organics and used without further purification. Anhydrous solvents were prepared with 4 Å molecular sieves. NMR spectra were recorded on a Varian INOVA-600 (600 MHz for $^1$H, 151 MHz for $^{13}$C), INOVA-500 (500 MHz for $^1$H and 125 MHz for $^{13}$C), and INOVA-400 (400 MHz for $^1$H, 100 MHz for $^{13}$C) instruments. Flash chromatography was performed using a Teledyne ISCO CombiFlash system.

Step 1. (9R)-hydroxydec-1-ene

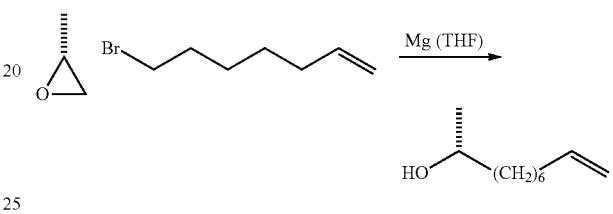

A solution of 7-bromoheptene (300 μg, 2 mmol) in dry THF (1 mL) was added drop wise to magnesium (240 mg, activated with iodine) in THF (500 μL). After stirring at RT for 1 hour the Grignard solution was transferred, cooled to −40° C. and treated with CuI (30 mg, 158 μmol). After stirring for 1 minute, (R)-propylene oxide (100 μL, 2 mmol) in THF (500 μL) was added and the solution stirred for 1.5 hours. The reaction was quenched with NH$_4$Cl (1 mL), extracted with diethyl ether, dried over Na$_2$SO$_4$, and concentrated in vacuum. Flash column chromatography on silica gel using an ethyl acetate-hexane gradient (0 to 20%) afforded (8R)-hydroxydec-1-ene (56 mg, 359 μmol, 18% yield) as a colorless liquid. $^1$H NMR (600 MHz, chloroform-d): δ 1.18 (3H, d, J=6.2 Hz), 1.25-1.50 (10H, m), 2.01-2.07 (2H, m), 3.76-3.82 (1H, m), 4.91-4.95 (1H, m), 4.97-5.01 (1H, m), 5.81 (1H, ddt, J=17.1 Hz, 10.4 Hz, 6.7 Hz).

Step 2. (9R)-(3'R,5'R-dibenzoyloxy-6'S-methyl-(2H)-tetrahydropyran-2-yloxy)-dec-1-ene

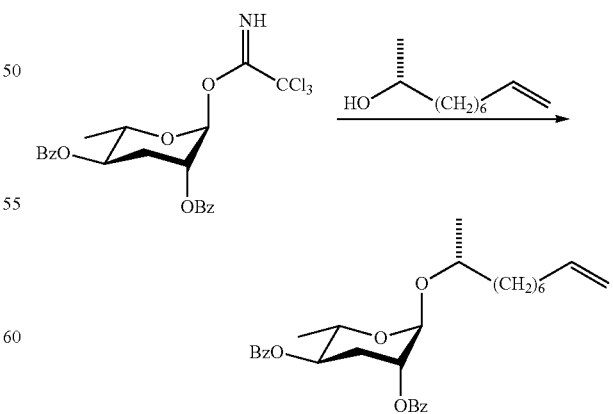

A solution of 2,4-di-O-benzoyl-ascarylose (Jeong et al. (2005) Nature 433:541-545) (139 mg, 390 μmol) in dry DCM (3 mL) was treated with trichloroacetonitrile (84 μL)

and DBU (5 µL). After stirring at room temperature for 30 minutes, the solution was concentrated in vacuum. Flash column chromatography on silica gel using a mixture of ethyl acetate in hexane (20%) afforded (3'R,5'R-dibenzoyloxy-6'S-methyl-(2H)-tetrahydropyran-2-yloxy)-1-(2,2,2-trichloroacetimide) (152 mg, 302 µmol, 78%) as a colorless oil. A solution of 2,4-di-O-benzoyl-ascarylose-1-(2,2,2-trichloroacetimide) (152 mg, 302 µmol) in dry DCM (3 mL) at 0° C. was treated with (9R)-hydroxydec-1-ene (55 mg, 350 µmol) and trimethylsilyloxytriflate (5 After 3 hours the solution was washed with saturated aqueous NaHCO₃ solution (0.5 mL), dried over Na₂SO₄ and concentrated in vacuum. Flash column chromatography on silica gel using a ethyl acetate-hexane gradient (5 to 20%) afforded (9R)-(3'R,5'R-dibenzoyloxy-6'S-methyl-(2H)-tetrahydropyran-2-yloxy)-dec-1-ene (91.1 mg, 184 µmol, 61%) as a colorless oil. $^1$H NMR (400 MHz, chloroform-d): δ 1.20 (3H, d, J=6.1 Hz), 1.30 (3H, d, J=6.1 Hz), 1.33-1.72 (10H, m), 2.09 (2H, m), 2.23 (1H, ddd, J=13.5 Hz, J=11.4 Hz, J=2.9 Hz), 2.44 (1H, m), 3.87 (1H, m), 4.15 (1H, dq, J=9.8 Hz, J=6.1 Hz), 4.95 (1H, ddt, J=10.2 Hz, J=2.2 Hz, J=1.3 Hz), 4.98 (1H, s.br), 5.02 (1H, ddt, J=17.1, Hz. J=2.2 Hz, J=1.6 Hz), 5.17 (1H, s.br), 5.21 (1H, ddd, J=10.3 Hz, J=4.6 Hz), 5.83 (1H, ddt, J=17.1 Hz, J=10.3 Hz, J=6.8 Hz), 7.45-7.51 (4H, m), 7.57-7.62 (2H, m), 8.06 (2H, m), 8.13 (2H, m); $^{13}$C NMR (100 MHz, chloroform-d): δ 17.84, 19.14, 25.65, 28.84, 29.08, 29.38, 29.68, 33.76, 37.08, 66.89, 70.62, 71.21, 72.53, 93.72, 114.20, 128.38, 129.55, 129.80, 129.82, 129.96, 133.12, 133.17, 139.01, 165.59, 165.72.

Step 3. Ethyl (10R)-(3'R,5'R-dibenzoyloxy-6'S-methyl-(2H)-tetrahydropyran-2-yloxy)-undec-2-enoate

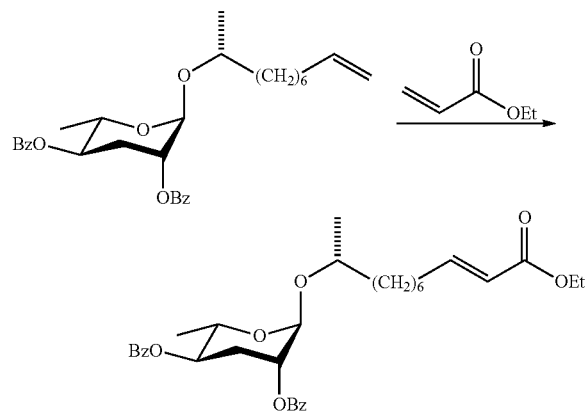

A solution of (9R)-(3'R,5'R-dibenzoyloxy-6'S-methyl-(2H)-tetrahydropyran-2-yloxy)-dec-1-ene (62 mg, 125 µmol) and ethyl propenoate (66 mg, 626 mol) in DCM (5 mL) was treated with 1.4-benzoquinone (1.4 mg, 13 mol) and Grubbs-II catalyst (5.3 mg, 6.3 mol). After stirring at 40° C. for 15 hours, the reaction was filtered through a pad of silica using DCM: ethyl acetate (3:1). Flash column chromatography on silica gel using a ethyl acetate-hexanes gradient (10 to 50%) afforded ethyl (10R)-(3'R,5'R-dibenzoyloxy-6'S-methyl-(2H)-tetrahydropyran-2-yloxy)-undec-2-enoate (55 mg, 97 mol, 78%) as a colorless oil. $^1$H NMR (400 MHz, chloroform-d): δ 1.19 (3H, d, J=6.1 Hz), 1.27 (3H, t, J=7.1 Hz), 1.28 (3H, d, J=6.3 Hz), 1.33-1.70 (10H, m), 2.16-2.26 (3H, m), 2.38-2.46, (1H, m), 3.84 (1H, m), 4.07-4.15 (1H, m), 4.17 (2H, q, J=7.1 Hz), 4.95 (1H, s.br), 5.12-5.23 (2H, m), 5.78-5.85 (1H. m), 6.97 (1H, dt, J=15.6 Hz, 7.0 Hz), 7.42-7.50 (4H, m), 7.55-7.62 (2H, m), 8.01-8.06 (2H, m), 8.09-8.14 (2H, m). $^{13}$C NMR (100 MHz, chloroform-d): δ 14.42, 18.03, 19.30, 25.78, 28.16, 29.28, 29.53, 29.87, 32.32, 37.23, 60.29, 67.09, 70.80, 71.38, 72.78, 93.93, 117.65, 121.44, 128.58, 129.73, 129.98, 129.99, 130.13, 133.32, 133.38, 149.44, 165.80, 165.93, 166.89.

Step 4. (10R)-(3'R,5'R-dihydroxy-6'S-methyl-(2H)-tetrahydropyran-2-yloxy)-undec-2-enoic acid (ascr #17)

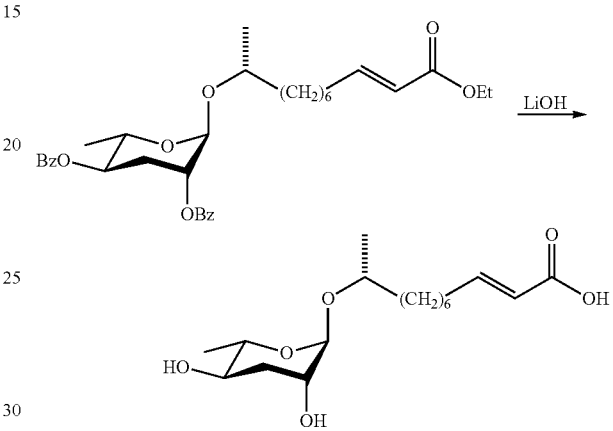

A solution of ethyl (10R)-(3'R,5'R-dibenzoyloxy-6'S-methyl-(2H)-tetrahydropyran-2-yloxy)-undec-2-enoate (55 mg, 97 µmol) in THF (1 mL) was added to a solution of lithium hydroxide (48 mg, 2 mmol) in water (380 µL) and 1,4-dioxane (2 mL). After stirring at 67° C. for 3 hours the mixture was neutralized with acetic acid and concentrated in vacuum. Flash column chromatography on silica gel using a methanol-dichloromethane gradient (0 to 30%) afforded (10R)-(3'R,5'R-dihydroxy-6'S-methyl-(2H)-tetrahydropyran-2-yloxy)-undec-2-enoic acid(ascr #17)(25.2 mg, 76.4 µmol, 79%) as a colorless oil. $^1$H NMR (500 MHz, methanol-d₄): δ 1.12 (3H, d, J=6.1 Hz), 1.21 (3H, d, J=6.3 Hz), 1.33-1.60 (10H, m), 1.76 (1H, ddd, J=13.3 Hz, J=11.4 Hz, J=3.1 Hz), 1.95 (1H, dt.br, J=13.1 Hz, J=4.1 Hz), 2.23 (2H, ddt, J=7.3 Hz, J=1.7 Hz, J=7.6 Hz), 3.52 (1H, ddd, J=11.3 Hz, J=9.5 Hz, J=4.6 Hz), 3.63 (1H, dq, J=9.3 Hz, J=6.4 Hz), 3.71 (1H, m), 3.78 (1H, m), 4.64 (1H, s.br), 5.80 (1H, dt, J=15.7 Hz, J=1.4 Hz), 6.95 (1H, dt, J=15.6 Hz, J=7.0 Hz); $^{13}$C NMR (100 MHz, methanol-d₄): δ 18.27, 19.53, 26.95, 29.40, 30.40, 30.61, 33.29, 36.09, 38.51, 68.45, 70.10, 71.30, 72.62, 97.67, 122.75, 151.25, 170.37.

Step 5. (10R)-(3'R,5'R-dihydroxy-6'S-methyl-(2H)-tetrahydropyran-2-yloxy)-undecanoic acid (ascr #18)

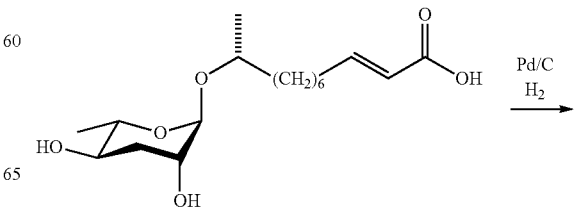

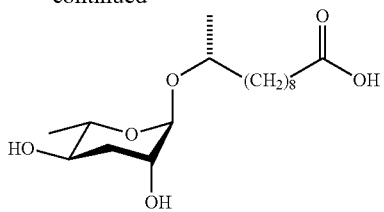

A solution of (10R)-(3'R,5'R-dihydroxy-6'S-methyl-(2H)-tetrahydropyran-2-yloxy)-undec-2-enoic acid (5 mg, 104 µmol) in methanol (1 mL) was treated with Pd/C (10% w/w) and hydrogenated for 14 hours. The solution was filtered and concentrated in vacuum to afford (10R)-(3'R,5'R-dihydroxy-6'S-methyl-(2H)-tetrahydropyran-2-yloxy)-undecanoic acid (4.4 mg, 76.4 µmol, 73%) as a colorless oil. $^1$H NMR (500 MHz, methanol-$d_4$): δ 1.12 (H, d, J=6.1 Hz), 1.21 (3H, d, J=6.3 Hz), 1.33-1.60 (14H, m), 1.76 (1H, ddd, J=13.3 Hz, J=11.4 Hz, J=3.1 Hz), 1.95 (1H, dt.br, J=13.1 Hz, J=4.1 Hz), 2.27 (2H, t, J=7.6 Hz), 3.52 (1H, ddd, J=11.3 Hz, J=9.5 Hz, J=4.6 Hz), 3.63 (1H, dq, J=9.3 Hz, J=6.4 Hz), 3.71 (1H, m), 3.78 (1H, m), 4.64 (1H, s.br); $^{13}$C NMR (100 MHz, methanol-$d_4$): δ 18.11, 19.37, 26.40, 26.88, 30.37, 30.48, 30.61, 30.67, 35.97, 38.42, 68.34, 69.99, 71.17, 72.51, 97.56, 178.6.

Several publications and patent documents are cited throughout the specification in order to describe the state of the art to which this invention pertains. Each of these citations is incorporated herein by reference as though set forth in full.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of protecting a plant from a pathogen, the method comprising contacting the plant and/or its immediate environment with an effective amount of a formulated blend comprising: a first ingredient comprising an ascaroside, and a second ingredient comprising a side-chain shortened analog of the ascaroside, wherein a mass ratio of the analog to the ascaroside is at least 5:1.

2. The method of claim 1, wherein said ratio is at least 10:1.

3. The method of claim 1, wherein said ascaroside is ascr #18.

4. The method of claim 3, wherein said second ingredient comprises a side-chain shortened analog of ascr #18.

5. The method of claim 4, wherein said side-chain shortened analog is at least one of ascr #9, ascr #10, and ascr #1.

6. The method of claim 5, wherein said side-chain shortened analog is ascr #9.

7. The method of claim 5, wherein said side-chain shortened analog is ascr #10.

8. The method of claim 5, wherein said side-chain shortened analog is ascr #1.

9. The method of claim 1, wherein said method further comprises chemically synthesizing at least one of the ascaroside or the side-chain shortened analog.

10. The method of claim 1, wherein said method further comprises producing at least one of the ascaroside of the side-chain shortened analog by fermentation.

11. The method of claim 1, wherein said pathogen is selected from the group consisting of a nematode, a virus, a bacteria, a fungus, an insect, and an oomycete.

12. A method of protecting a plant from a pathogen, the method comprising contacting the plant and/or its immediate environment with an effective amount of a first ingredient comprising an ascaroside, and a second ingredient comprising a side-chain shortened analog of the ascaroside, wherein a mass ratio of the analog to the ascaroside is at least 5:1.

13. The method of claim 12, wherein said mass ratio of the analog to the ascaroside is at least 10:1.

14. The method of claim 12, wherein said first and said second ingredients are applied at the same time.

15. The method of claim 12, wherein said first and second ingredients are applied sequentially.

16. A composition comprising an effective amount of a formulated blend comprising: a first ingredient comprising an ascaroside, and a second ingredient comprising a side-chain shortened analog of the ascaroside, wherein a mass ratio of the analog to the ascaroside is at least 5:1, and wherein said composition further comprises an agronomically acceptable carrier.

17. The composition of claim 16, wherein the mass ratio of the analog to the ascaroside is at least 10:1.

18. The composition of claim 16, wherein said ascaroside is ascr #18.

19. The composition of claim 18, wherein said side-chain shortened analog is at least one of ascr #9, ascr #10, and ascr #1.

20. The composition of claim 19, wherein said side-chain shortened analog is ascr #9.

21. A seed treated with the composition of claim 16.

22. A plant or plant root treated with the composition of claim 16.

* * * * *

UNITED STATES PATENT AND TRADEMARK OFFICE
CERTIFICATE OF CORRECTION

PATENT NO. : 12,376,588 B2
APPLICATION NO. : 17/603021
DATED : August 5, 2025
INVENTOR(S) : Murli Manohar and Frank Schroeder Page 1 of 1

It is certified that error appears in the above-identified patent and that said Letters Patent is hereby corrected as shown below:

In the Specification

At Column 1, Line 10, please delete:
"12217687"

And insert therefor:
--2017-67013-26535--

Signed and Sealed this
Sixteenth Day of September, 2025

Coke Morgan Stewart
*Acting Director of the United States Patent and Trademark Office*

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: AtPR-1 F primer

<400> SEQUENCE: 1
tcgtctttgt agctcttgta ggtg                                           24

<210> SEQ ID NO 2
<211> LENGTH: 23
<212> TYPE: DNA
<213> ORGANISM: Artificial Sequence
<220> FEATURE:
<223> OTHER INFORMATION: AtPR-1 R primer

<400> SEQUENCE: 2
tagattctcg taatctcagc tct                                            23

<210> SEQ ID NO 3
<211> LENGTH: 20
<212> TYPE: DNA
<213> ORGANISM: Artificial Sequence
<220> FEATURE:
<223> OTHER INFORMATION: AtPDF1.2-F primer

<400> SEQUENCE: 3
tcatggctaa gtttgcttcc                                                20

<210> SEQ ID NO 4
<211> LENGTH: 19
<212> TYPE: DNA
<213> ORGANISM: Artificial Sequence
<220> FEATURE:
<223> OTHER INFORMATION: AtPDF1.2-R primer

<400> SEQUENCE: 4
aatacacacg attagcacc                                                 19

<210> SEQ ID NO 5
<211> LENGTH: 19
<212> TYPE: DNA
```

```
<213> ORGANISM: Artificial Sequence
<220> FEATURE:
<223> OTHER INFORMATION: AtFRK1-fw primer

<400> SEQUENCE: 5
tgcagcgcaa ggactagag                                                    19

<210> SEQ ID NO 6
<211> LENGTH: 20
<212> TYPE: DNA
<213> ORGANISM: Artificial Sequence
<220> FEATURE:
<223> OTHER INFORMATION: AtFRK1-rv primer

<400> SEQUENCE: 6
atcttcgctt ggagcttctc                                                   20

<210> SEQ ID NO 7
<211> LENGTH: 20
<212> TYPE: DNA
<213> ORGANISM: Artificial Sequence
<220> FEATURE:
<223> OTHER INFORMATION: AtPHI-fw primer

<400> SEQUENCE: 7
ttggtttaga cgggatggtg                                                   20

<210> SEQ ID NO 8
<211> LENGTH: 20
<212> TYPE: DNA
<213> ORGANISM: Artificial Sequence
<220> FEATURE:
<223> OTHER INFORMATION: AtPHI-rv primer

<400> SEQUENCE: 8
actccagtac aagccgatcc                                                   20

<210> SEQ ID NO 9
<211> LENGTH: 27
<212> TYPE: DNA
<213> ORGANISM: Artificial Sequence
<220> FEATURE:
<223> OTHER INFORMATION: AtUBQ-fw primer

<400> SEQUENCE: 9
ggccttgtat aatccctgat gaataag                                           27

<210> SEQ ID NO 10
<211> LENGTH: 27
<212> TYPE: DNA
<213> ORGANISM: Artificial Sequence
<220> FEATURE:
<223> OTHER INFORMATION: AtUBQ-rv primer

<400> SEQUENCE: 10
aaagagataa caggaacgga aacatag                                           27

<210> SEQ ID NO 11
<211> LENGTH: 19
<212> TYPE: DNA
<213> ORGANISM: Artificial Sequence
<220> FEATURE:
<223> OTHER INFORMATION: AtPR4-F primer

<400> SEQUENCE: 11
ctggaccgcc ttctgcggg                                                    19
```

```
<210> SEQ ID NO 12
<211> LENGTH: 21
<212> TYPE: DNA
<213> ORGANISM: Artificial Sequence
<220> FEATURE:
<223> OTHER INFORMATION: AtPR4-R primer

<400> SEQUENCE: 12
agcctccgtt gctgcattgg t                                        21

<210> SEQ ID NO 13
<211> LENGTH: 19
<212> TYPE: DNA
<213> ORGANISM: Artificial Sequence
<220> FEATURE:
<223> OTHER INFORMATION: AtAOS-F primer

<400> SEQUENCE: 13
tcttctcttc gccacgtgc                                           19

<210> SEQ ID NO 14
<211> LENGTH: 22
<212> TYPE: DNA
<213> ORGANISM: Artificial Sequence
<220> FEATURE:
<223> OTHER INFORMATION: AtAOS-R primer

<400> SEQUENCE: 14
ggttatgaac ttgatgaccc gc                                       22

<210> SEQ ID NO 15
<211> LENGTH: 19
<212> TYPE: DNA
<213> ORGANISM: Artificial Sequence
<220> FEATURE:
<223> OTHER INFORMATION: AtLOX2-F primer

<400> SEQUENCE: 15
ttgctcgcca gacacttgc                                           19

<210> SEQ ID NO 16
<211> LENGTH: 19
<212> TYPE: DNA
<213> ORGANISM: Artificial Sequence
<220> FEATURE:
<223> OTHER INFORMATION: AtLOX2-R primer

<400> SEQUENCE: 16
gggatcacca taaacggcc                                           19
```